United States Patent
Collazo et al.

(10) Patent No.: US 9,345,578 B2
(45) Date of Patent: May 24, 2016

(54) BICRUCIATE RETAINING TIBIAL IMPLANT SYSTEM

(71) Applicant: Stryker Corporation, Kalamazoo, MI (US)

(72) Inventors: Carlos E. Collazo, Old Greenwich, CT (US); Evan Leibowitz, Linden, NJ (US); Rahul Ramachandran, Dover, NJ (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 14/182,562

(22) Filed: Feb. 18, 2014

(65) Prior Publication Data

US 2014/0243990 A1      Aug. 28, 2014

Related U.S. Application Data

(60) Provisional application No. 61/767,954, filed on Feb. 22, 2013.

(51) Int. Cl.
| | |
|---|---|
| *A61F 2/38* | (2006.01) |
| *A61B 17/15* | (2006.01) |
| *A61B 17/17* | (2006.01) |
| *A61B 17/16* | (2006.01) |
| *A61F 2/30* | (2006.01) |

(52) U.S. Cl.
CPC .............. *A61F 2/389* (2013.01); *A61B 17/157* (2013.01); *A61B 17/1675* (2013.01); *A61B 17/1764* (2013.01); *A61B 17/1604* (2013.01); *A61F 2002/30131* (2013.01); *A61F 2002/30688* (2013.01); *A61F 2002/30892* (2013.01)

(58) Field of Classification Search
CPC ........ A61F 2/385; A61F 2/3868; A61F 2/389
See application file for complete search history.

(56) References Cited

U.S. PATENT DOCUMENTS

| | | |
|---|---|---|
| 3,798,679 A | 3/1974 | Ewald |
| 3,816,855 A | 6/1974 | Saleh |

(Continued)

FOREIGN PATENT DOCUMENTS

| | | |
|---|---|---|
| EP | 0306744 A2 | 3/1989 |
| EP | 1011542 A1 | 6/2000 |

(Continued)

OTHER PUBLICATIONS

BioPro, Equalizer Modular Total Knee Replacement, date not known.

(Continued)

*Primary Examiner* — Yashita Sharma
*Assistant Examiner* — Daniel Bissing
(74) *Attorney, Agent, or Firm* — Lerner, David, Littenberg, Krumholz & Mentlik, LLP

(57) ABSTRACT

A bicruciate retaining tibial implant baseplate includes a tibial baseplate with medial and lateral condylar portions configured to receive bearing inserts. The baseplate includes an anterior bridge connecting the medial and lateral portions. A posterior wall of the anterior bridge may be angled to provide downward force on a correspondingly angled anterior portion of the tibial eminence when the baseplate is implanted. A method of preparing the tibia for implant includes a punch tower and punch guide configured to both cut the anterior tibial eminence and provide protection to the tibial eminence during resection of the proximal tibia.

12 Claims, 32 Drawing Sheets

(56) References Cited

U.S. PATENT DOCUMENTS

| | | |
|---|---|---|
| 3,869,731 A | 3/1975 | Waugh et al. |
| 4,207,627 A | 6/1980 | Cloutier |
| 4,586,933 A | 5/1986 | Shoji et al. |
| 4,711,639 A | 12/1987 | Grundei |
| 4,769,040 A | 9/1988 | Wevers |
| 4,822,362 A | 4/1989 | Walker et al. |
| 5,037,439 A | 8/1991 | Albrektsson et al. |
| 5,137,536 A | 8/1992 | Koshino |
| 5,171,283 A | 12/1992 | Pappas et al. |
| 5,282,868 A | 2/1994 | Bahler |
| 5,509,934 A | 4/1996 | Cohen |
| 5,658,341 A | 8/1997 | Delfosse |
| 5,702,464 A | 12/1997 | Lackey et al. |
| 5,755,801 A | 5/1998 | Walker et al. |
| 5,824,103 A | 10/1998 | Williams |
| 5,879,394 A | 3/1999 | Ashby et al. |
| 6,258,127 B1 | 7/2001 | Schmotzer |
| 6,387,131 B1 | 5/2002 | Miehlke et al. |
| 6,436,145 B1 | 8/2002 | Miller |
| 6,482,209 B1 | 11/2002 | Engh et al. |
| 6,558,421 B1 | 5/2003 | Fell et al. |
| 6,652,588 B2 | 11/2003 | Hayes, Jr. et al. |
| 6,679,914 B1 | 1/2004 | Gabbay |
| 6,699,291 B1 | 3/2004 | Augoyard et al. |
| 6,896,702 B2 | 5/2005 | Collazo |
| 6,969,393 B2 | 11/2005 | Pinczewski et al. |
| 7,060,101 B2 | 6/2006 | O'Connor et al. |
| 7,066,963 B2 | 6/2006 | Naegerl |
| 7,115,131 B2 | 10/2006 | Engh et al. |
| 7,261,740 B2 | 8/2007 | Tuttle et al. |
| 7,294,149 B2 | 11/2007 | Hozack et al. |
| 7,458,933 B2 | 12/2008 | LeVahn et al. |
| 7,462,199 B2 | 12/2008 | Justin et al. |
| 7,578,850 B2 | 8/2009 | Kuczynski et al. |
| 7,625,407 B2 | 12/2009 | Akizuki et al. |
| 7,635,390 B1 | 12/2009 | Bonutti |
| 7,695,519 B2 | 4/2010 | Collazo |
| 7,758,652 B2 | 7/2010 | Engh et al. |
| 7,766,969 B2 | 8/2010 | Justin et al. |
| 7,771,483 B2 | 8/2010 | Justin et al. |
| 7,771,484 B2 | 8/2010 | Campbell |
| 7,799,086 B2 | 9/2010 | Justin et al. |
| 7,828,852 B2 | 11/2010 | Bonutti |
| 8,066,776 B2 | 11/2011 | O'Connor et al. |
| 8,092,546 B2 | 1/2012 | Coon et al. |
| 8,105,387 B2 | 1/2012 | Barnett et al. |
| 8,114,165 B2 | 2/2012 | Rhodes et al. |
| 8,128,703 B2 | 3/2012 | Hazebrouck et al. |
| 8,137,407 B2 | 3/2012 | Todd et al. |
| 8,157,869 B2 | 4/2012 | Metzger et al. |
| 8,211,181 B2 | 7/2012 | Walker |
| 8,292,964 B2 | 10/2012 | Walker |
| 8,292,965 B2 | 10/2012 | Walker |
| 8,343,227 B2 | 1/2013 | Metzger et al. |
| 8,403,994 B2 | 3/2013 | Maloney et al. |
| 8,500,818 B2 | 8/2013 | Metzger et al. |
| 8,529,631 B2 | 9/2013 | Donno et al. |
| 8,568,486 B2 * | 10/2013 | Wentorf .................. A61F 2/389 623/20.28 |
| 8,574,304 B2 | 11/2013 | Wentorf et al. |
| 8,603,101 B2 | 12/2013 | Claypool et al. |
| 8,613,775 B2 | 12/2013 | Wentorf et al. |
| 8,911,501 B2 | 12/2014 | Irwin et al. |
| 2004/0025926 A1 * | 2/2004 | Gin .......................... A61H 3/02 135/68 |
| 2004/0030397 A1 | 2/2004 | Collazo |
| 2004/0138755 A1 | 7/2004 | O'Connor et al. |
| 2005/0283251 A1 | 12/2005 | Coon et al. |
| 2006/0004460 A1 | 1/2006 | Engh et al. |
| 2006/0195196 A1 | 8/2006 | Pendleton et al. |
| 2006/0212124 A1 | 9/2006 | Siebel |
| 2006/0265079 A1 | 11/2006 | D'Alessio |
| 2007/0010890 A1 | 1/2007 | Collazo |
| 2007/0173858 A1 | 7/2007 | Engh et al. |
| 2007/0203582 A1 | 8/2007 | Campbell |
| 2008/0119941 A1 | 5/2008 | Seo et al. |
| 2009/0187251 A1 | 7/2009 | Justin et al. |
| 2009/0270995 A1 | 10/2009 | Rhodes et al. |
| 2009/0319048 A1 | 12/2009 | Shah et al. |
| 2010/0016980 A1 | 1/2010 | Donno et al. |
| 2010/0131071 A1 | 5/2010 | O'Connor et al. |
| 2010/0280624 A1 | 11/2010 | Engh et al. |
| 2010/0305575 A1 | 12/2010 | Wilkinson et al. |
| 2010/0305710 A1 | 12/2010 | Metzger et al. |
| 2010/0305711 A1 | 12/2010 | McKinnon et al. |
| 2010/0331847 A1 | 12/2010 | Wilkinson et al. |
| 2010/0331848 A1 | 12/2010 | Smith et al. |
| 2010/0331991 A1 | 12/2010 | Wilkinson et al. |
| 2011/0015749 A1 | 1/2011 | Engh et al. |
| 2011/0066248 A1 | 3/2011 | Ries et al. |
| 2011/0066249 A1 | 3/2011 | Justin et al. |
| 2011/0082559 A1 | 4/2011 | Hartdegen et al. |
| 2011/0098824 A1 | 4/2011 | Jukes et al. |
| 2011/0190898 A1 * | 8/2011 | Lenz et al. ............ 623/20.32 |
| 2011/0264097 A1 | 10/2011 | Hodorek et al. |
| 2012/0035736 A1 | 2/2012 | O'Connor et al. |
| 2012/0078262 A1 | 3/2012 | Pinczewski et al. |
| 2012/0179266 A1 | 7/2012 | Collazo |
| 2012/0209394 A1 | 8/2012 | Bojarski et al. |
| 2012/0316563 A1 | 12/2012 | Metzger et al. |
| 2012/0330429 A1 | 12/2012 | Axelson, Jr. et al. |
| 2013/0006375 A1 | 1/2013 | Metzger et al. |
| 2013/0024001 A1 | 1/2013 | Wentorf et al. |
| 2013/0046385 A1 | 2/2013 | Hartdegen et al. |
| 2013/0131817 A1 | 5/2013 | Parisi et al. |
| 2013/0131819 A1 | 5/2013 | Parisi et al. |
| 2013/0173010 A1 * | 7/2013 | Irwin .................. A61F 2/38 623/20.32 |
| 2013/0204383 A1 | 8/2013 | Wentorf |
| 2013/0245777 A1 | 9/2013 | Jerry |
| 2013/0289731 A1 | 10/2013 | Katerberg et al. |
| 2013/0345820 A1 | 12/2013 | Maloney et al. |
| 2014/0025175 A1 | 1/2014 | Wentorf et al. |
| 2014/0025176 A1 | 1/2014 | Wentorf et al. |
| 2014/0025177 A1 | 1/2014 | Wentorf et al. |
| 2014/0067076 A1 | 3/2014 | Collazo |

FOREIGN PATENT DOCUMENTS

| | | |
|---|---|---|
| FR | 2676916 A1 | 12/1992 |
| WO | 9858603 A1 | 12/1998 |
| WO | 0076428 A1 | 12/2000 |
| WO | 2006012370 A2 | 2/2006 |
| WO | 2009158318 A1 | 12/2009 |
| WO | 2010006677 A1 | 1/2010 |
| WO | 2010138836 A2 | 12/2010 |
| WO | 2010138841 A2 | 12/2010 |
| WO | 2010138850 A2 | 12/2010 |
| WO | 2010138854 A2 | 12/2010 |
| WO | 2010138857 A2 | 12/2010 |
| WO | 2011094540 A2 | 8/2011 |
| WO | 2012178031 | 12/2012 |
| WO | 2013101582 | 7/2013 |
| WO | 2013148954 | 10/2013 |

OTHER PUBLICATIONS

Freeman-Swanson Total Knee Prosthesis, Vitallium Alloy Femoarl Component, 1978.

Howmedica, Inc. Cruciate-Condylar Total Knee Surgical Technique, 1979.

Howmedica, Inc. The Howmedica Kinematic Knee System, 1980.

International Search Report and Written Opinion, PCT/US2012/0020719, dated Mar. 19, 2012.

Townley Total Knee Prosthesis, Vitallium Alloy Femoral Component, 1978.

Partial International Search Report for Application No. PCT/US2014/017664 dated Apr. 16, 2014.

International Search Report and Written Opinion for Application No. PCT/US2014/017664 dated Jun. 6, 2014.

International Search Report and Written Opinion for International Application No. PCT/US2012/070531, mailed May 27, 2013, 17 pages.

(56) References Cited

OTHER PUBLICATIONS

Townley, Charles O., Total Knee Arthroplasty: A Personal Retrospecteive and Prospective Review, Clinical Orthopaedics and Related Research, No. 236, 1988, 15 pages.

Pritchett, James W., BioPro: Equalizer Modular Total Knee Replacement, available at least as early as 1999, 19 pages.

Townley, Charles 0., Total Knee Arthroplasty: A Personal Retrospective and Prospective Review, Clinical Orthopaedics and Related Research, No. 236, 1988, 15 pages.

* cited by examiner

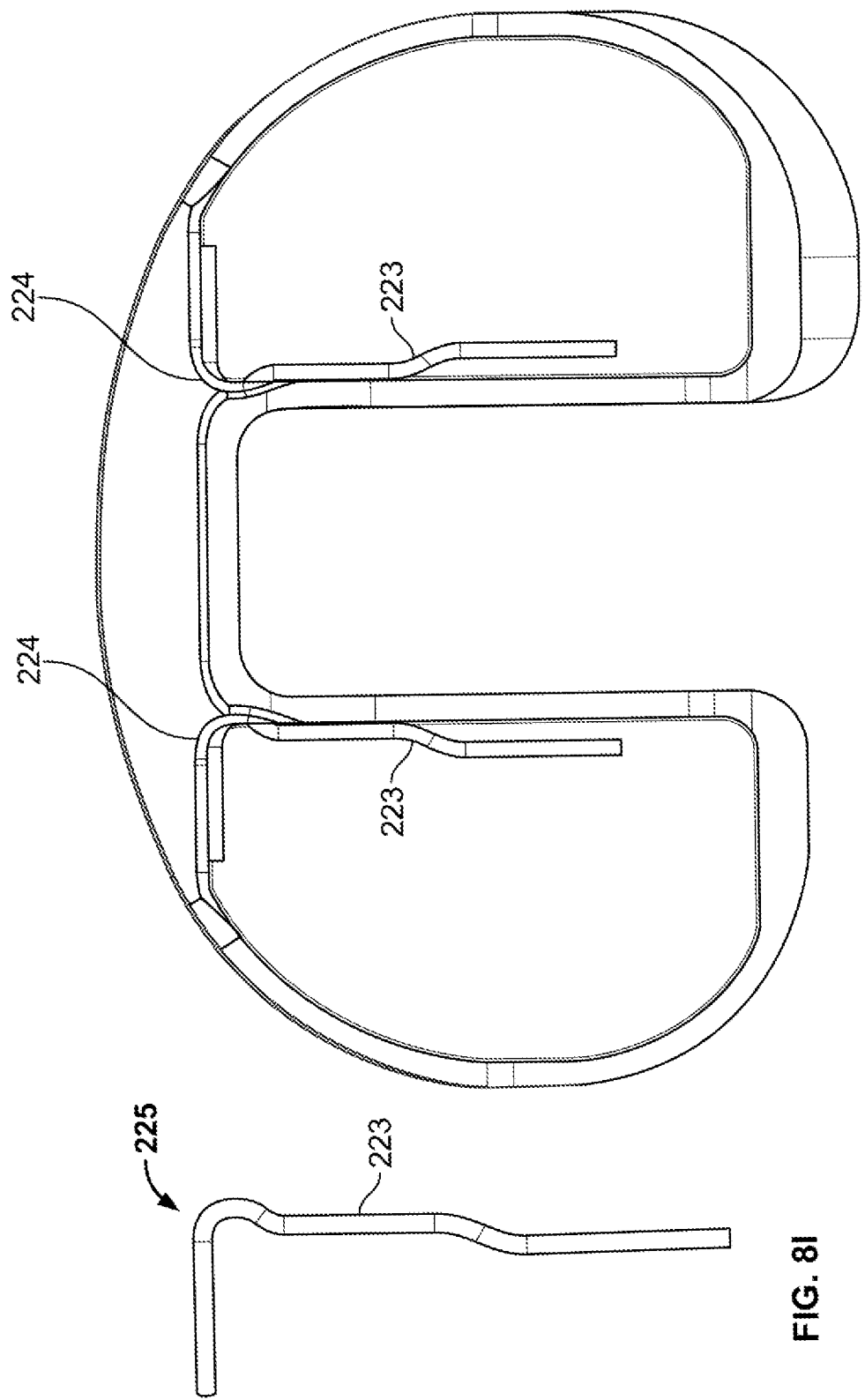

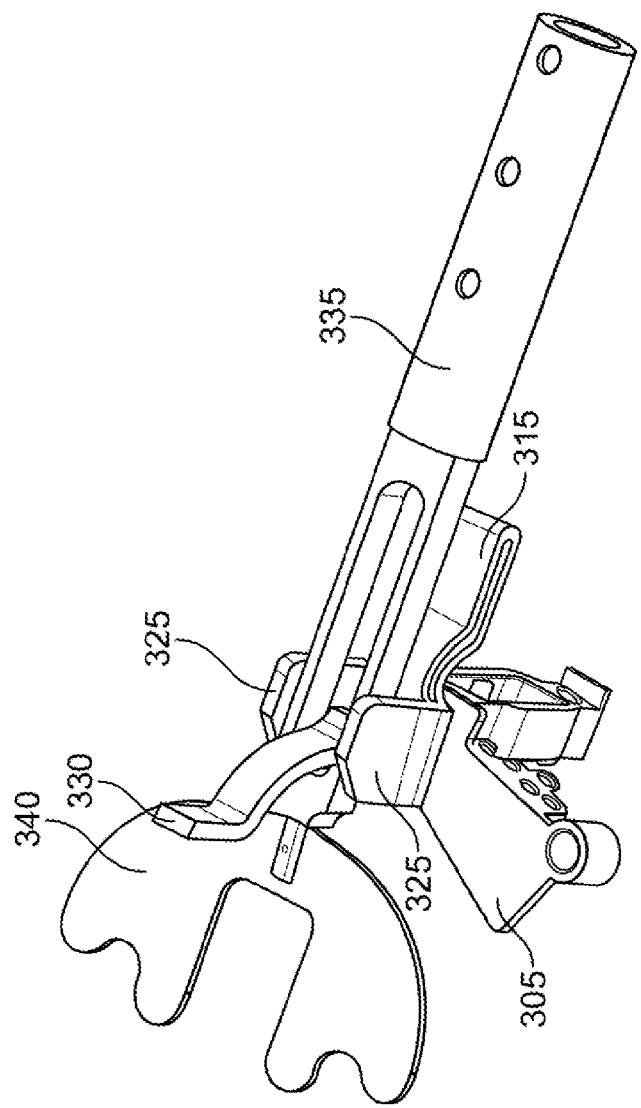
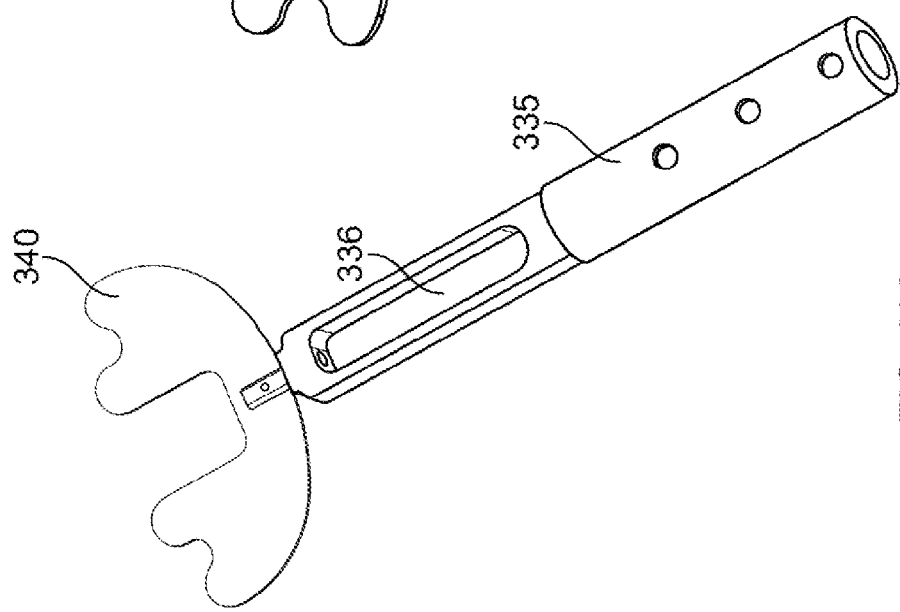
FIG. 11B
FIG. 11A

BICRUCIATE RETAINING TIBIAL IMPLANT SYSTEM

CROSS-REFERENCE TO RELATED APPLICATIONS

The present application claims the benefit of the filing date of U.S. Provisional Patent Application No. 61/767,954 filed Feb. 22, 2013, the disclosure of which is hereby incorporated herein by reference.

BACKGROUND OF THE INVENTION

Bicruciate retaining (BCR) implants are known and have been in use since at least the early 1970s. Their use allows the preservation of both cruciate ligaments, the anterior cruciate ligament (ACL) and the posterior cruciate ligament (PCL). Early designs included implants that were bicompartmental, i.e., the articular cartilage of the distal femur and the proximal tibia was replaced to alleviate pain and restore function, but not the patella and corresponding trochlear groove. However, starting in the late 1970s, the use of BCR implants started to decline as the introduction of the tricompartmental knees gained popularity.

There is a never ending quest to improve/restore natural knee kinematics following total knee replacement especially with the baby boomer generation getting surgery at a much younger age and still expecting a return to normal, active lifestyle activities such as golf, biking, hiking, and skiing. However, modern day implants still have limitations in offering natural joint kinematics. For example, a common misnomer in what the surgical community presently refers to as a Cruciate Retaining (CR) knee, the PCL is preserved but not the ACL. Therefore, the best that this knee can ever be is equivalent to an ACL deficient knee. In a Posterior Stabilized (PS) knee, both cruciates are sacrificed and only a partial function of the PCL is restored through the use of a cam on the femoral component and a post on the tibial insert. Therefore, since knees with compromised or torn cruciates are intrinsically unstable, it is believed that preserving both cruciates would improve joint stability and function following Total Knee Arthroplasty (TKA).

BCR implants may be indicated for use in situations which are similar to standard PCL-retaining TKA devices, or which are unique to BCR implants. For example, BCR indications for use which are similar to standard PCL-retaining devices may include painful, disabling joint disease of the knee resulting from non-inflammatory degenerative joint disease (including osteoarthritis, traumatic arthritis or avascular necrosis), rheumatoid arthritis or post-traumatic arthritis. Additional indications include post-traumatic loss of knee joint configuration and function; moderate varus, valgus, or flexion deformity in which the ligamentous structures can be returned to adequate function and stability; revisions of previous unsuccessful knee replacement or other procedure; fracture of the distal femur and/or proximal tibia that cannot be stabilized by standard fracture management techniques; and situations in which the PCL is intact, functional, and healthy. BCR implants may additionally be used in situations retaining the ACL for closer-to-natural stability, or even in situations with a deficient ACL.

Some drawbacks of prior art BCR baseplate designs are avulsion (tearing away) of the tibial eminence, and less than optimal instrumentation and surgical techniques, making surgery more challenging. Improved tibial implants and methods of implantation would thus be desirable.

BRIEF SUMMARY OF THE INVENTION

In one embodiment, a bicruciate retaining tibial baseplate has a superior surface, a bone contacting surface, a lateral condylar portion, and a medial condylar portion. The medial condylar portion is spaced from the lateral condylar portion, defining an eminence opening therebetween. A bridge connects the medial and lateral condylar portions at an anterior end of the baseplate. A keel extends inferiorly from the bone contacting surface of the baseplate. The keel extends from the lateral condylar portion across the bridge to the medial condylar portion. A lateral fixation peg is proximate a lateral end of the keel and extends inferiorly from the bone contacting surface. A medial fixation peg is proximate a medial end of the keel and extends inferiorly from the bone contacting surface.

The bridge of the baseplate may include an angled posterior wall such that a portion of a first side of the angled posterior wall extends farther posteriorly than a portion of a second side of the angled posterior wall. The angled posterior wall is configured to contact an angled surface of a tibial eminence when implanted. The angled posterior wall of the baseplate may be angled between approximately 5-45 degrees with respect to a resected surface of the tibia, preferably between approximately 15-25 degrees.

The bicruciate retaining tibial implant baseplate may also include a medial insert configured to be inserted into the medial condylar portion of the baseplate and a lateral insert configured to be inserted into the lateral condylar portion of the baseplate. At least one of the medial and lateral inserts may include a spring connected to a pin, the spring biasing the pin. The pin is configured to mate with a corresponding pin aperture in a portion of the baseplate to lock the insert to the baseplate. At least one of the medial and lateral inserts may include a relief portion on a medial side of the insert, the relief portion increasing in size from an anterior portion of the insert toward a posterior portion of the insert.

The medial and lateral condylar portions of the baseplate may each have a superior surface, a bone contacting surface, and an anterior-posterior dimension. The anterior-posterior dimension of the medial condylar portion may be larger than the anterior-posterior dimension of the lateral condylar portion. The anterior-posterior dimension of the medial condylar portion may be between approximately 1 and approximately 6 millimeters larger than the anterior-posterior dimension of the lateral condylar portion, preferably between approximately 3 and approximately 5 millimeters.

In another embodiment, a method of preparing a tibia of a patient for implantation of a bicruciate retaining tibial implant comprising fixing a tibial resection guide to the tibia, creating a medial sagittal cut in a proximal surface of the tibia medial to a tibial eminence, and creating a lateral sagittal cut in the proximal surface of the tibia lateral to the tibial eminence. The method may also include positioning first and second feet of a punch guide in the medial and lateral sagittal cuts, and inserting a punch through a slot in the punch guide. The punch is driven into the tibial eminence; and a transverse cut is created in the proximal surface of the tibia while the first foot of the punch guide remains in the medial sagittal cut, the second foot of the punch guide remains in the lateral sagittal cut, and the punch remains in the tibial eminence.

The step of driving the punch into the tibial eminence may also include driving the punch into the tibial eminence at an angle. The angle may be between approximately 0 and 45 degrees relative to a longitudinal axis of the tibia, preferably between 15 and 25 degrees.

The method may also include positioning an anterior chamfer cut guide on a resected surface of the tibia after the step of creating the transverse cut. It may be evaluated whether an anterior portion of the tibial eminence protrudes beyond an angled cutting surface of the anterior chamfer cut guide. If the anterior portion of the tibial eminence is determined to protrude beyond the angled cutting surface of the anterior chamfer cut guide, anterior portion of the tibial eminence may be cut using the angled cutting surface as a guide.

In another embodiment of the invention, a tibial eminence punch system includes a punch guide configured to be coupled to a tibial resection guide, and a punch tower having a proximal portion and a distal portion. The punch guide defines a slot corresponding to a shape of, and is configured to receive, the distal portion of the punch tower. The distal portion of the punch guide may include a hollow space defined by a generally straight medial side wall, a generally straight lateral side wall, and a rounded anterior wall connecting the medial side wall to the lateral side wall.

BRIEF DESCRIPTION OF THE DRAWINGS

FIGS. 8I-J illustrate multiple views of another embodiment of a locking feature of the insert and baseplate.

FIG. 11A illustrates a perspective view of a modular handle and template.

FIG. 11B illustrates the modular handle and template of FIG. 11A coupled to the tibial resection guide in an unlocked position.

DETAILED DESCRIPTION

In the following description, certain directional terms are used. Generally, "proximal" refers to a location closer to the heart, while "distal" refers to a location farther from the heart. "Superior" refers to a location closer to the head while "inferior" refers to a location closer to the feet. "Medial" refers to a location closer to the midline of the body, while "lateral" refers to a location farther away from the midline of the body. "Anterior" refers to a location closer to the front of the body, while "posterior" refers to a location closer to the back of the body. With reference to the figures provided, identical numbers generally refer to similar or identical features. When ranges of values are provided, it should be understood that all values within the provided range are included, as well as all ranges within the range provided. For example, a range of 2 to 8 includes the values of 3 and 4, as well as the ranges of 4 to 7, as well as 3 to 5.

Generally, the description below relates to primary and/or revision TKA procedures. More specifically, the description below relates to a tibial implant, a method of preparing the tibia, and a method of implanting the tibial implant onto the tibia. It is understood that this procedure generally is undertaken during a surgery in which the femur is also prepared for a femoral. The procedure may also be undertaken simultaneously with other related procedures, such as patellar implantations, as is known in the art.

Figure 1A:
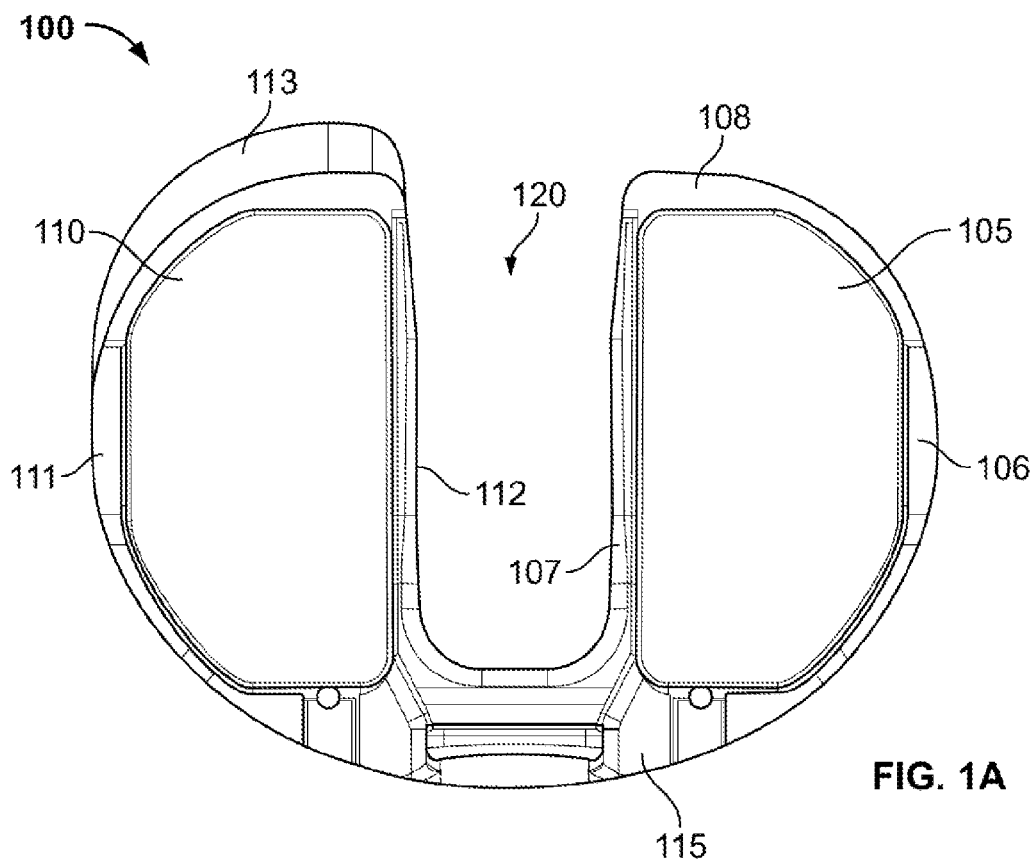
FIGS. 1A-B illustrate top plan and top perspective views of a tibial baseplate according to an embodiment of the invention.
Figure 1B:
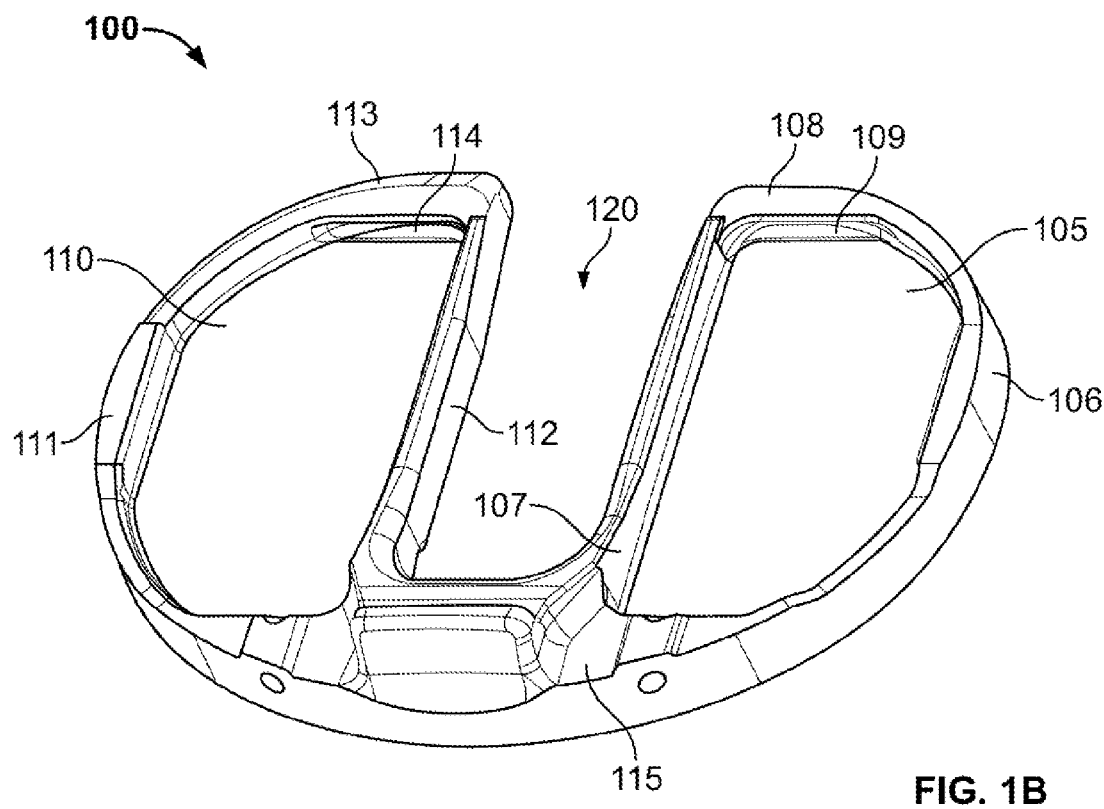

Referring to FIGS. 1A-B, there is shown a top view and top perspective view, respectively, (looking at the superior surface when implanted) of a tibial baseplate or tray 100 according to an embodiment of the invention. Baseplate 100 includes a lateral condylar portion 105 and a medial condylar portion 110. Portions 105, 110 are designed to receive a bearing insert 200 (illustrated in FIG. 5), such as an ultra high molecular weight polyethylene (UHMWPE) bearing component. Lateral and medial condylar portions 105, 110 are connected by a bridge section 115. Lateral and medial condylar portions 105, 110 are preferably recessed and surrounded by a raised wall portion 106 laterally and 111 medially to locate the bearing insert 200. Likewise, U-shaped eminence opening 120 is defined by lateral wall 107 and medial wall 112. Posterior walls 108 and 113 define the posterior end of the recesses in the lateral and medial condylar portions 105, 110, respectively. Undercut grooves 109, 114 may be located adjacent walls 108, 113 at the superiorly facing surface of condylar portions 105, 110 to allow the bearing inserts 200 to be snapped into their respective condylar portions 105, 110. In one embodiment, the bearing insert 200 (illustrated in FIG. 8B) includes a posterior groove 230 that snaps into a respective undercut groove 109, 114.

Figure 2A:
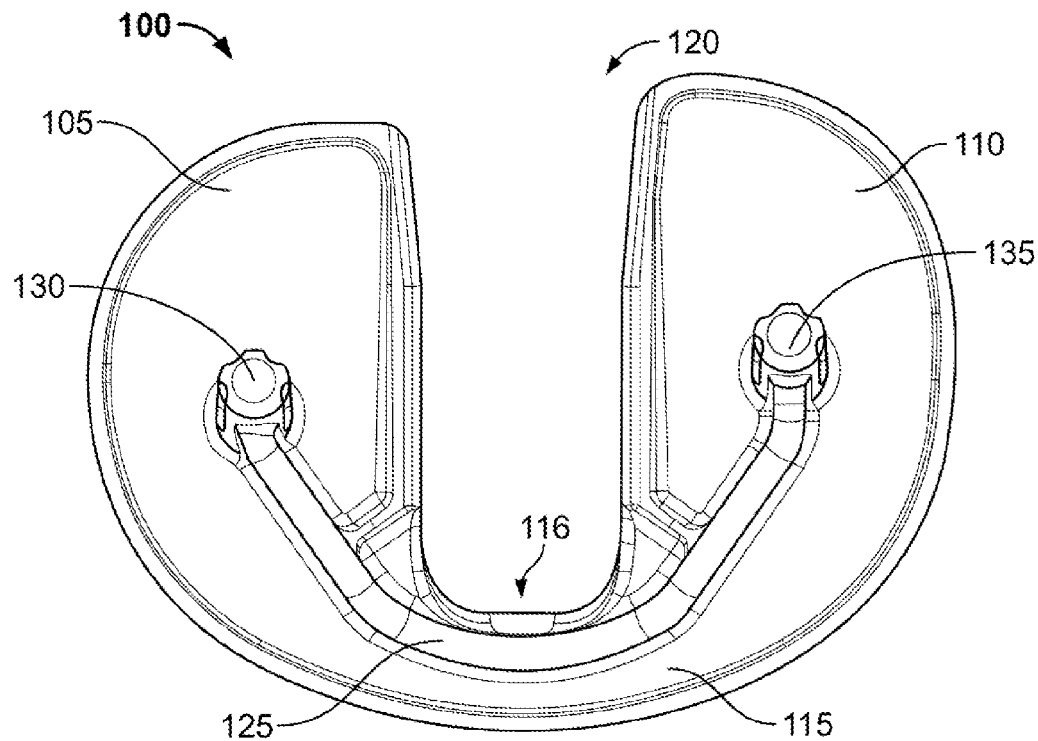
FIGS. 2A-B illustrate bottom plan and bottom perspective views of the tibial baseplate of FIGS. 1A-B.
Figure 2B:
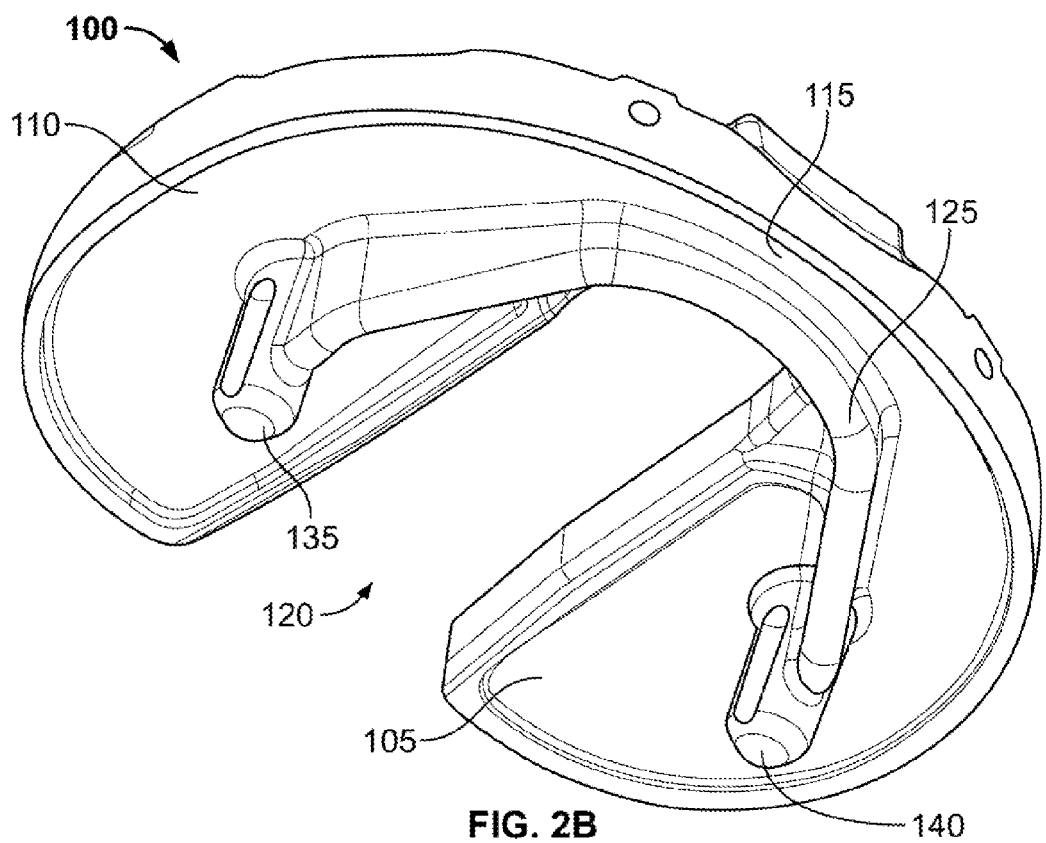
Figure 3A:
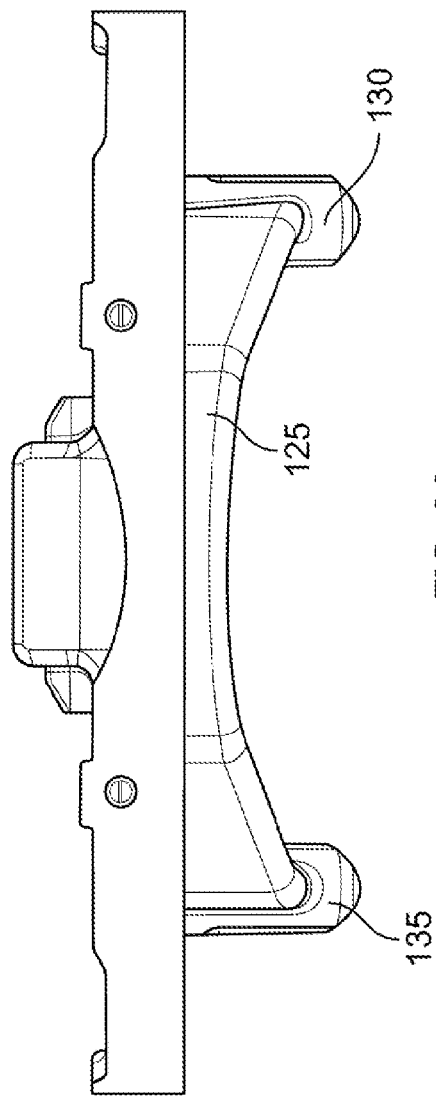
FIGS. 3A-B illustrate front plan and rear plan views of the tibial baseplate of FIGS. 1A-B.
Figure 3B:
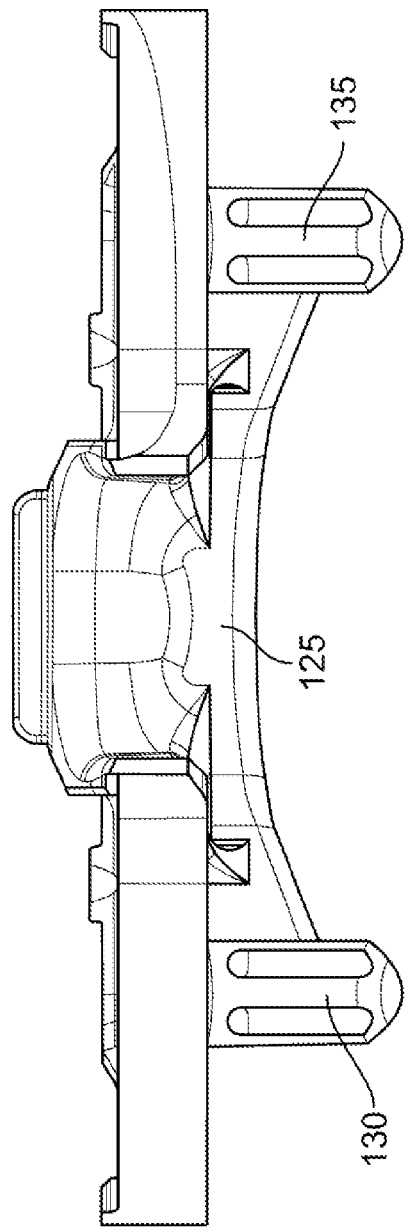

Referring to FIGS. 2A-2B, there is shown a bottom view and bottom perspective view, respectively, of baseplate 100 including the bone contacting surface. As seen, lateral portion 105 and medial portion 110 are separated by eminence opening 120 and are connected by anterior bridge 115 at the anterior end of the baseplate 100. The bottom surface of the baseplate 100 may include a keel 125 extending inferiorly. In the illustrated embodiment, keel 125 is generally "U," "V," or "C" shaped and extends from the lateral condylar portion 105, across the bottom of bridge 115, to the medial condylar portion 110.

Figure 4A:
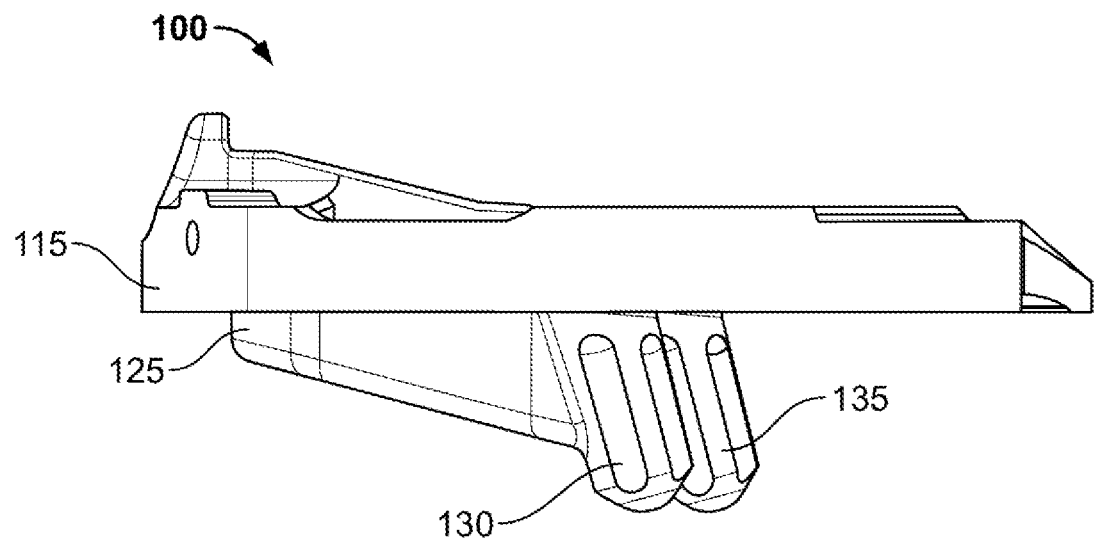
FIG. 4A illustrates a side plan view of the tibial baseplate of FIGS. 1A-B.
Figure 4B:
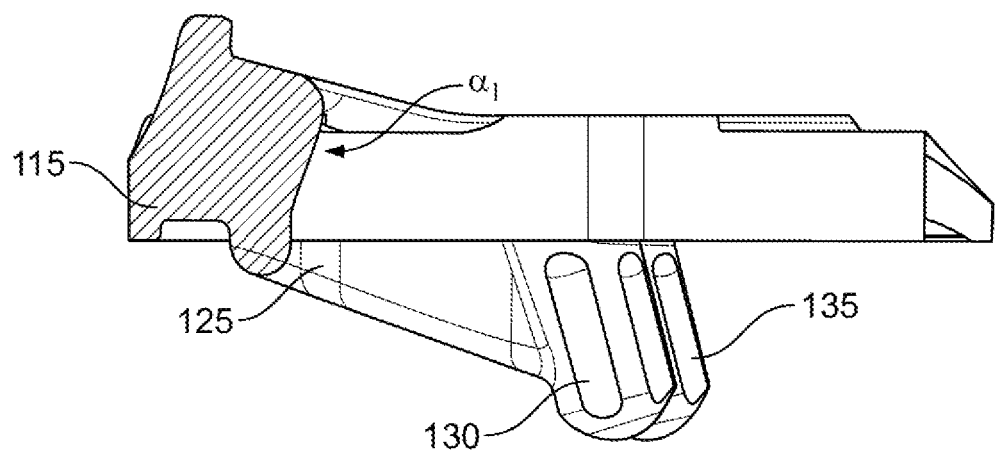
FIG. 4B illustrates a side plan view in partial cross-section of the tibial baseplate of FIGS. 1A-B.

A posterior wall of bridge 115 may be angled relative to the resected surface of the tibia 300, as best illustrated in FIG. 4B. In one embodiment, the posterior wall 116 of the bridge 115 has an angle $\alpha_1$ between approximately 5° and 45°, preferably approximately 20°. The angle $\alpha_1$ of the posterior wall 116 of bridge 115 is such that a superior portion of the posterior wall 116 extends further posteriorly than an inferior portion of the posterior wall 116. In this configuration, the posterior wall 116 of the bridge 115 generally exerts a downward force on an anterior portion of the tibial eminence 345 (discussed further below with reference to FIGS. 17-20A). This may be particularly useful, for example, in providing a downward force to counteract the tendency of the ACL to lift the tibial eminence 345. Additionally, the angle $\alpha_1$ of the posterior wall 116 of the bridge 115 minimizes the amount of tibial bone that must be removed anterior to the tibial eminence 345 which helps maximize the bone strength. Further, the angle $\alpha_1$ of the posterior wall 116 of the bridge 115 allows cement to act as a buttress against the tibial eminence 345.

In certain embodiments, the thickness of the anterior bridge 115 may range from approximately 0.390 inches (9.91 millimeters) to approximately 0.475 inches (12.07 millimeters). In one embodiment, the baseplate 100 comes in three groups of sizes with respect to the thickness of the anterior bridge 315. The thickness of the anterior bridge 115 in the smallest group may be approximately 0.398 inches (12.07 millimeters). The thickness of the anterior bridge 115 in the largest group may be approximately 0.465 inches (11.81 millimeters). The thickness of the anterior bridge 115 in the middle group may be approximately 0.450 inches (11.43 millimeters). These sizes, and all other sizes listed herein, are merely illustrative of exemplary embodiments of the current invention and may be altered to fit the specific needs of a particular embodiment of the invention.

The width of the eminence opening 120 may be partially dependent on the size of the baseplate 100 being used. For example, a larger sized baseplate 100 generally would have an eminence opening 120 that is larger in the medial-lateral (ML) dimension. The size of the eminence opening 120 may be dictated by different factors. For example, a smaller eminence opening 120, with correspondingly more surface area on the baseplate 100, may allow for more area of contact with a corresponding femoral component of the implant. However, this would leave less space for the tibial eminence 345 and less clearance for the ACL and PCL. The converse is also true, wherein a larger eminence opening 120 would leave more space for the tibial eminence 345 and more clearance for the ACL and PCL, but would reduce the amount of surface area on the baseplate 100 available for a femoral component.

The width of the eminence opening 120 may represent between approximately 20% and 30% of the width of the baseplate 100 in the ML dimension. In one embodiment, the baseplate 100 comes in three groups of sizes with respect to the width of the eminence opening 120. For example, the width of the eminence opening 120 in the smallest group of baseplate 100 sizes may be approximately 0.700 inches (17.78 millimeters). The width of the eminence opening 120 in the largest group of baseplate 100 sizes may be approximately 0.780 inches (19.81 millimeters). The width of the eminence opening 120 in the middle three baseplate 100 sizes may be approximately 0.740 inches (18.80 millimeters). These sizes, and all other sizes listed herein, are merely illustrative of exemplary embodiments of the current invention and may be altered to fit the specific needs of a particular embodiment of the invention.

As best seen in FIGS. 2A-B and 4A-B, the posterior portions of keel 125 may extend further inferiorly than the anterior portion of keel 125. When implanted, the keel 125 of the baseplate 100 extends into the resected surface of the tibia 300. The variable cut height of the keel 125 helps to maximize the implant strength of the baseplate 100 while remaining shallow in the anterior-most portion of the tibia 300. This, in turn, helps to prevent anterior fracture as the keel 125 is near the cortical rim of the tibia 300. Another benefit of the shallow anterior keel 125 is that there is no stress riser anterior to the tibial eminence 345, which may further reduce the likelihood of anterior fracture. As seen for example in FIGS. 25C, 26C, and 27C, there is a relatively low thickness of tibial bone between the position of the keel 125 in the tibial keel recess 545 and the cortical wall of the tibia 300. This lack of thickness increases the likelihood of anterior fracture in this portion of the tibia 300, which is at least partially mitigated by the features of the keel 125 described herein.

In one embodiment, the keel 125 is perpendicular to the resection surface of the tibia 300 to maximize the strengthening effects of the keel 125 and to minimize the shear force delivered to the bone. In other embodiments, the keel 125 is angled up to 30° from perpendicular. The angle of the keel 125 results in the total height of the baseplate 100 from top to bottom being shorter than a baseplate 100 with a perpendicular keel. During surgery, the working space may be limited and this shorter dimension may make it easier for the surgeon to work with the limited space.

Additionally, the keel 125 may include ribs, struts, inward striations, outward striations, or any combination of these features. These additional features may aid in cementation and fixation of the keel 125 to the tibia 300 as well as adding to the strength of the baseplate 100 when implanted. Outward striations, for example, may also increase the strength of the baseplate 100 by virtue of the extra material forming the striations. Likewise, keel 125 may include bone ingrowth structures which promote growth of natural bone into their surfaces. Certain bone ingrowth structures may result in stress shielding, although this effect may be lessened in relatively shallow keels. Finally, the thickness of the keel 125 may range, for example, between about 5% and 20% of the surface area of the keel 125, preferably about 10%.

A lateral fixation peg 130 and medial fixation peg 135, best seen in FIGS. 3A-B and 4A-B, may be positioned at the lateral and medial ends of keel 125, respectively. Lateral peg 130 and medial peg 135 may be generally cylindrical and extend inferiorly from the bottom surfaces of the lateral and medial condylar portions 105, 110 respectively. Functionally, pegs 130, 135 help guide the baseplate 100 into the desired location in the prepared bone (bone preparation discussed more completely below with reference to FIGS. 9-27B). The pegs 130, 135 also help resist rotation between the baseplate 100 and the tibia 300 once implanted. The pegs 130, 135 may be angled, for example between approximately 10° and 45°, preferably approximately 15°. Although variations are possible, the pegs 130, 135 are preferably located generally at the midpoint of the anterior-posterior (AP) dimension of the lateral condylar portion 105 and the medial condylar portion 110, respectively, as best seen in FIGS. 2A-B. This location may help the lateral and medial condylar portions 105, 110 of the baseplate 100 accept loads applied to the baseplate 100 nearly equally.

In one embodiment, the width of the baseplate 100 in the ML direction varies depending on the size of the baseplate. For example, 8 differently sized baseplate may be used to attend to all or nearly all TKA procedures, with each baseplate 100 having a different width in the ML direction. Further, the dimension of the lateral condylar portion 105 in the AP direction may be different than the dimension of the medial condylar portion 110 in the AP direction, making each baseplate 100 asymmetric (i.e. specific to the right/left knee). This extended dimension is illustrated particularly clearly in FIGS. 1A and 2A. For example, the medial condylar portion 110 may be between approximately 0-6 millimeters larger in the AP direction than the lateral condylar portion 105. Preferably, the medial condylar portion 110 is between approximately 3-5 millimeters larger in the AP direction compared to the lateral condylar portion 105. The amount of extension of the medial condylar portion 110 in the AP direction may be dependent on the size of the baseplate 100. For example, the additional 3-5 millimeters may be spaced over differently sized baseplates 100, with the smallest baseplate 100 having the smallest extended dimension and the largest baseplate 100 having the largest extended dimension.

One benefit of the AP dimension extension for the medial condylar portion 110 includes maximized bone coverage, which may help with better load transfer. Other benefits include increased surface area and additional cement land to increase fixation strength. The periphery of the implant may also reach a larger extent of the cortical rim, which is preferred for load transfer. This is compared to other known baseplates, in which the AP dimension of the medial condylar portion of the baseplate lays in cancellous bone for most patients. This AP dimension extension also more correctly approximates the anatomical shape of the tibia. The anatomic periphery may also aid in setting internal/external alignment intraoperatively and during preoperative planning.

Figure 5:
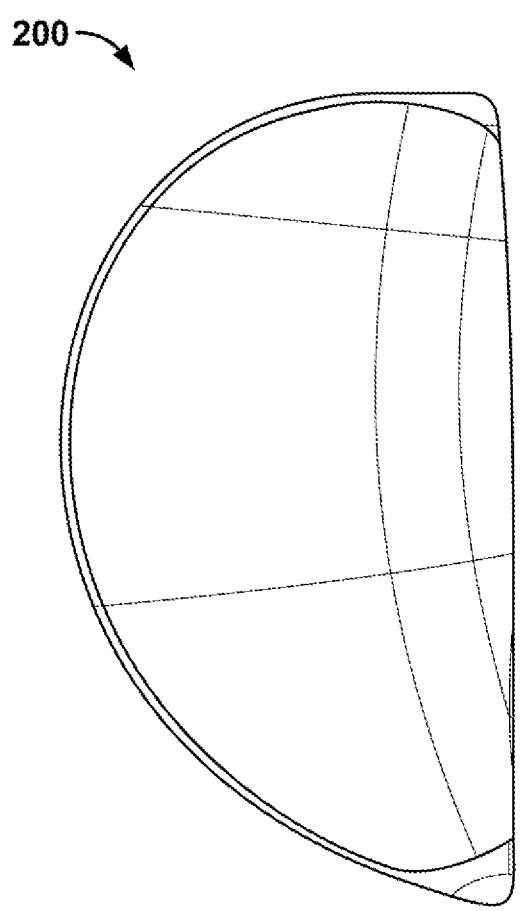
FIG. 5 illustrates a top plan view of a bearing insert according to an embodiment of the invention.

Now referring to FIG. 5, a top view of a bearing insert 200 according to an embodiment of the invention is illustrated. Inserts 200 provide a surface for a femoral component of the implant (not shown) to interact with. One insert 200 is coupled to the medial condylar portion 110 of the baseplate 100, and a second insert (not shown) is coupled to the lateral condylar portion 105 of the baseplate 100. In one embodiment, these inserts 200 may be symmetric. This embodiment may be preferred if the ACL is likely to rupture postoperatively. In another embodiment, the inserts 200 are asymmetric with regard to the AP/ML sizes and/or in geometric constraint. For example, the insert 200 on the medial side may be more constrained than a flatter insert 200 on the lateral side. This asymmetric configuration more closely imitates anatomic articulation and is preferred when the ACL remains functional postoperatively.

Figure 6A:
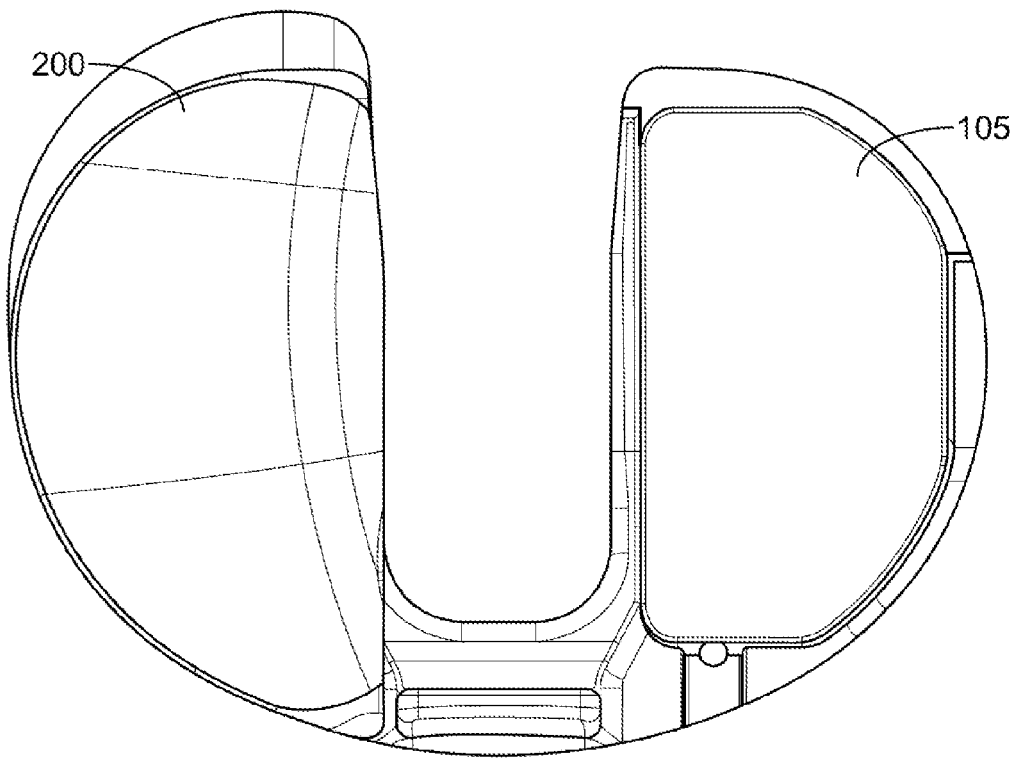
FIGS. 6A-B illustrate top plan and top perspective views of the insert of FIG. 5 coupled to the tibial baseplate of FIGS. 1A-B.
Figure 6B:
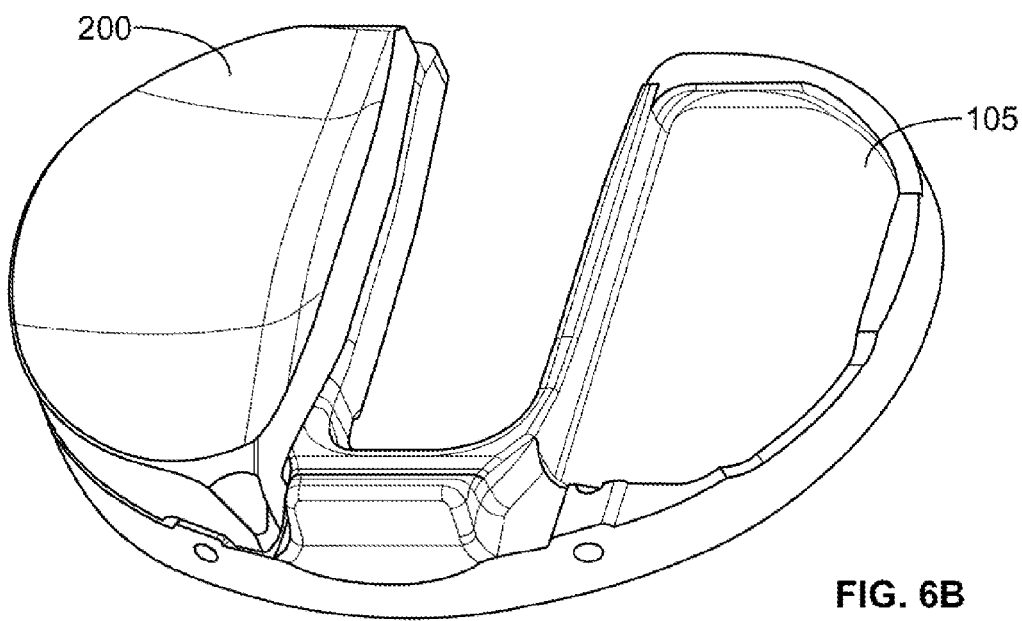

As illustrated in FIGS. 6A-B, the insert 200 locks into the baseplate 100. The insert 200 is dimensioned relative to the baseplate 100 such that the insert 200 may be press fit into the respective condylar portion of the baseplate 100 by hand. The press fit in the AP and ML directions, as well as additional optional locking mechanisms of the insert 200 (described below with reference to FIG. 7), resist disengagement of the insert 200 from the baseplate 100. Preferably, the insert 200 does not fully engage the baseplate 100 with press fitting until the insert 200 is between approximately 10% and 50% seated in the respective condylar portion of the baseplate 100. Preferably, the insert 200 fully engages the baseplate 100 when the insert 200 is approximately 20% seated in the respective condylar portion of the baseplate 100. This feature may allow a user to properly align the insert 200 with the respective condylar portion of the baseplate 100 before fully seating the insert 200. This feature may be achieved, for example, by providing an angled press fit relief 205, as seen in FIG. 8B, on the side of the insert 200 facing eminence opening 120. As the insert 200 is inserted into the baseplate, the press fit relief area 205 below the diagonal line in FIG. 8B causes the relieved portion of the insert 200 to not engage the baseplate 100 initially. As the insert 200 is inserted further, the area of the insert 200 above the relief area 205 (above the diagonal line in FIG. 8B), engages the baseplate 100.

Figure 7:
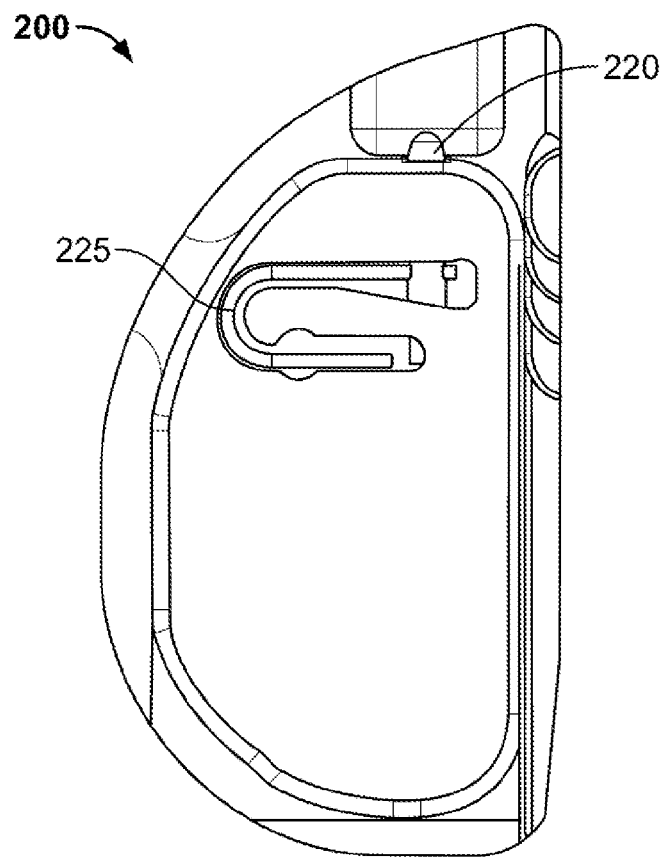
FIG. 7 illustrates a bottom plan view of a bearing insert with a locking pin and spring according to another embodiment of the invention.

Now referring to FIG. 7, a bottom view of the insert 200 is illustrated. In this embodiment, the bottom of insert 200 includes a locking mechanism in the form of a pin 220 and spring 225 on the anterior side of the insert 200. The spring 225 is generally "U" or "J" shaped and housed within a "U" or "J" shaped slot in the insert. One end of an anterior portion of the spring 225 traverses an aperture in the pin 220. This configuration causes the pin 220 to be biased toward the anterior portion of insert 200. The application of force on the pin 220 in the posterior direction causes the spring 225 to flex and allows the pin 220 to move posteriorly. During insertion of the insert 200 into the respective condylar portion of the baseplate 100, the pin 220 is forced to move posteriorly. Once the insert 200 is partially or fully seated in the baseplate 100, the pin 220 aligns with a corresponding aperture in the baseplate 100, and the biased pin snaps into the corresponding aperture in the baseplate, locking the insert 200 in place.

Figure 8A:
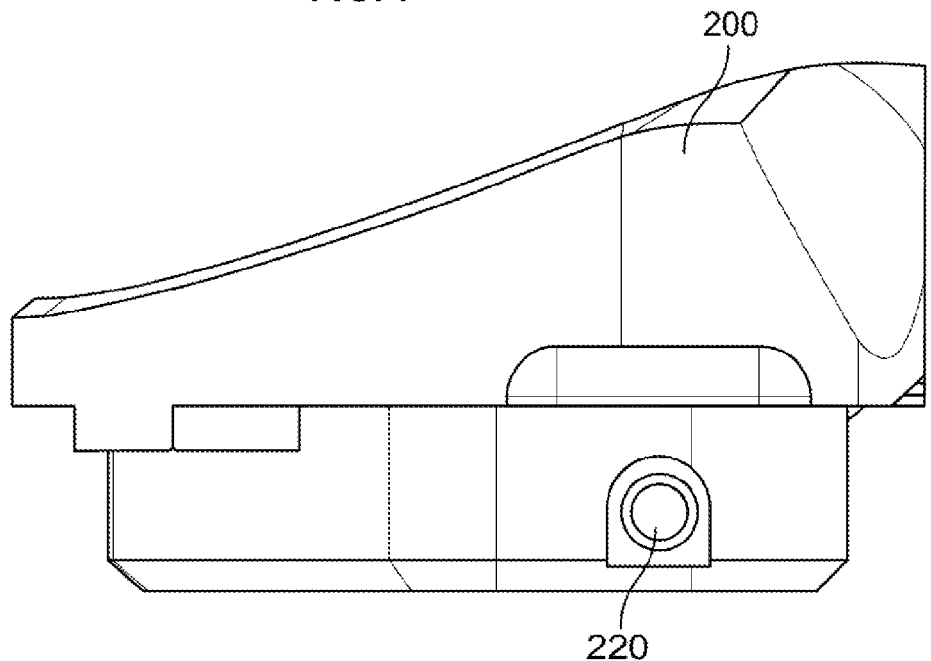
FIGS. 8A-C illustrate multiple views of the insert of FIG. 7.
Figure 8B:
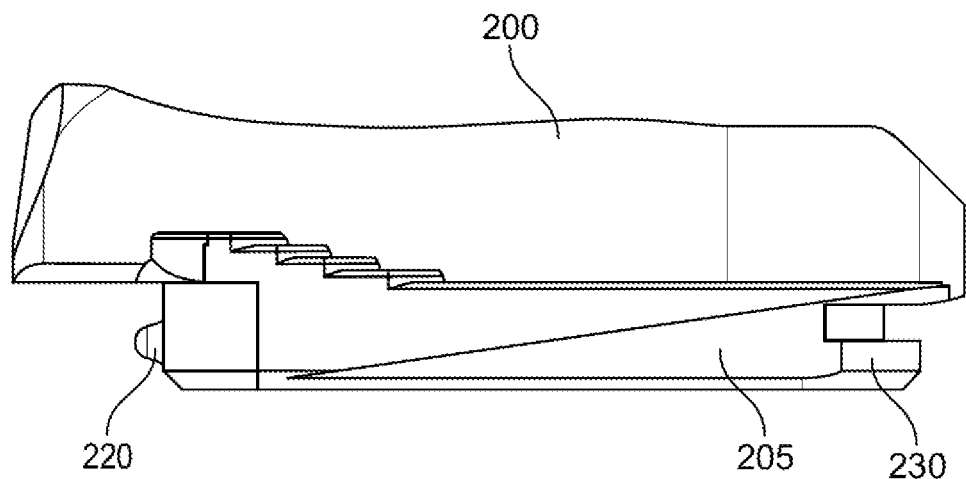
Figure 8C:
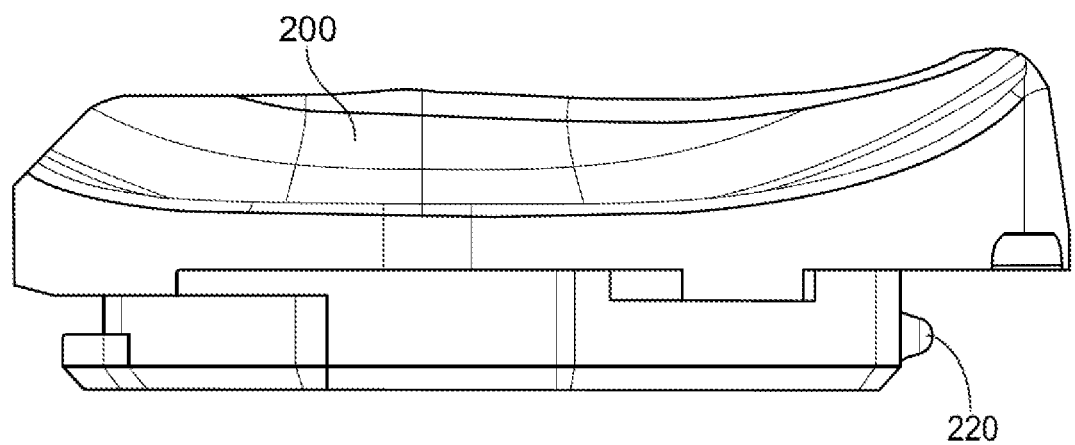
Figure 8D:
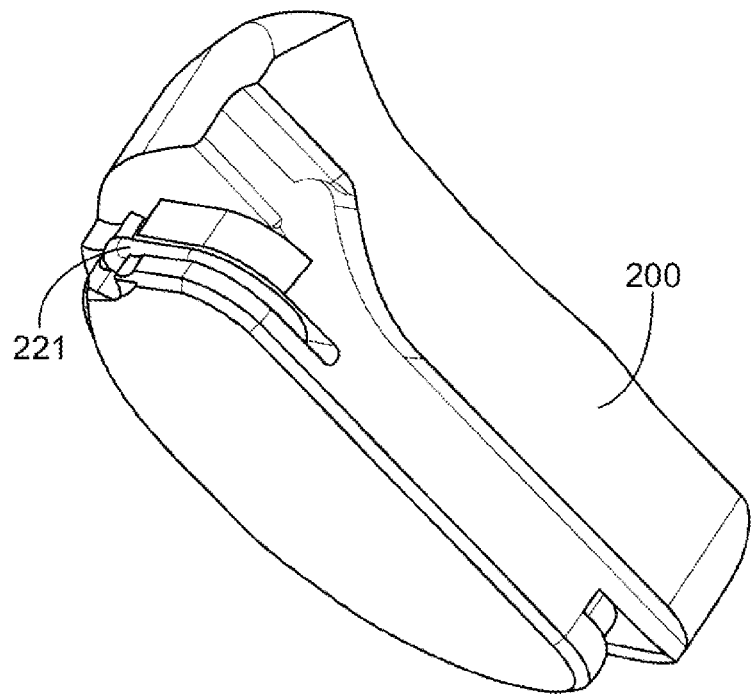
FIGS. 8D-H illustrate multiple views of an embodiment of a locking feature of the insert and baseplate.
Figure 8E:
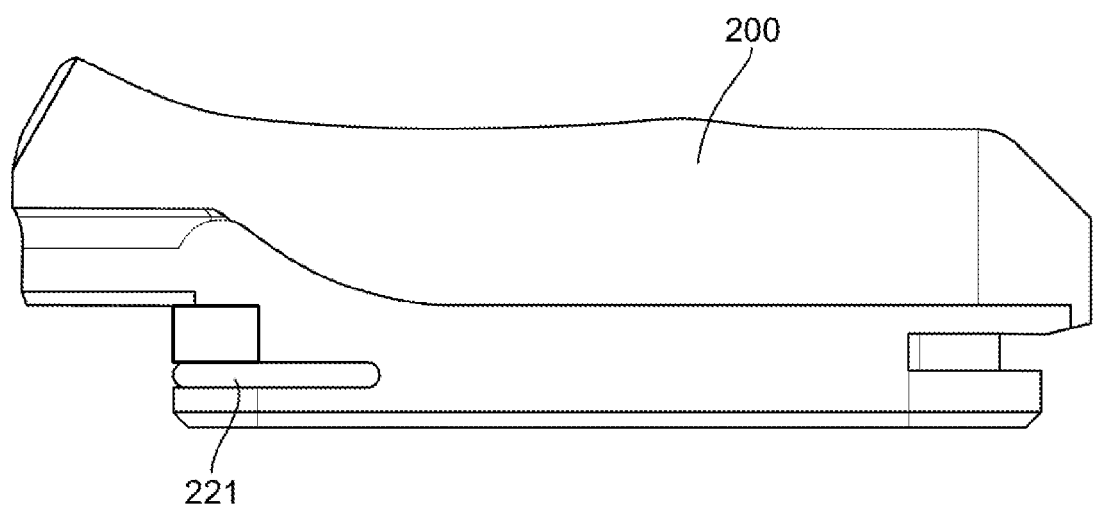

The locking feature is best illustrated in FIGS. 8A-C. The locking action, in addition to the press fit engagement of the insert 200 with the baseplate 100, may help resist the tendency of the insert to disengage or lift-off the baseplate 100 when force is applied, for example during deep flexion of the knee. In addition to helping lock the insert 200 in the baseplate 100, the pin 220 and spring 225 configuration allows the insert 200 to be removed from the baseplate 100 using a tool to engage the pin 200 to push the pin posteriorly and disengage with the baseplate 100. This unlocking action may allow the insert 200 to be removed from the baseplate without damaging the insert 200 or baseplate 100. In another embodiment, the pin may take the form of an anterior tab (not illustrated). The benefit of a tab-style pin is that the load on the locking mechanism could be dispersed over the larger area of a tab compared to the illustrated pin 220.

Figure 8F:
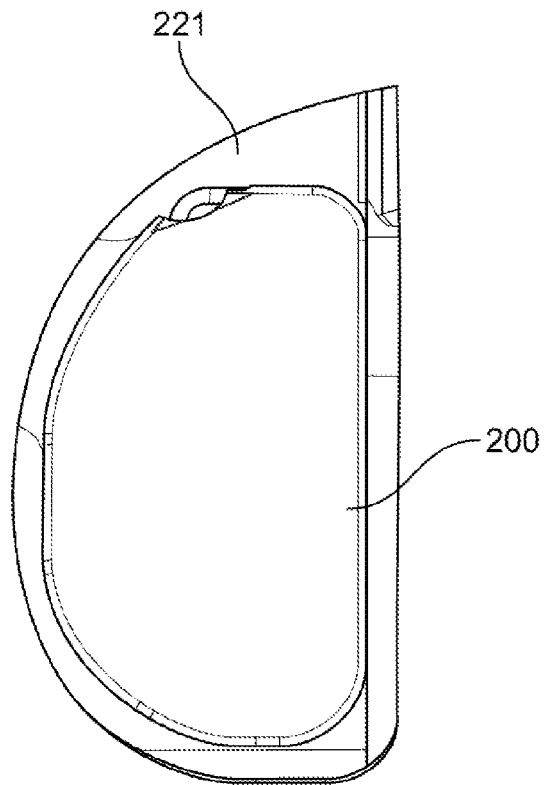
Figure 8G:
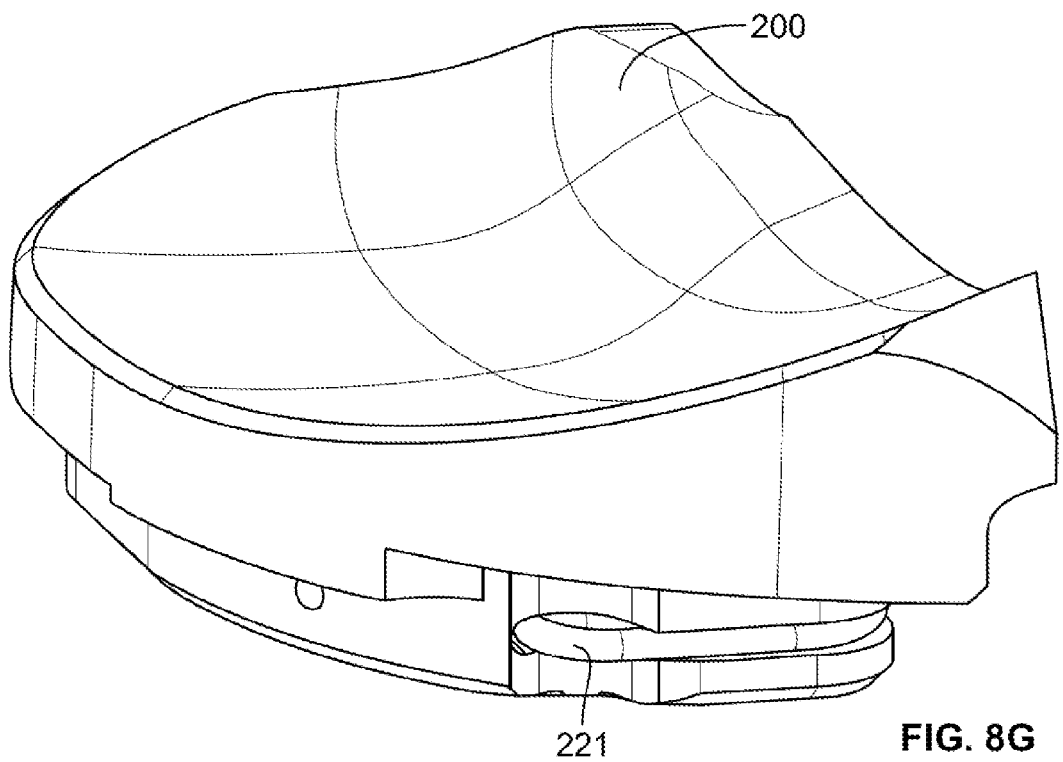
Figure 8H:
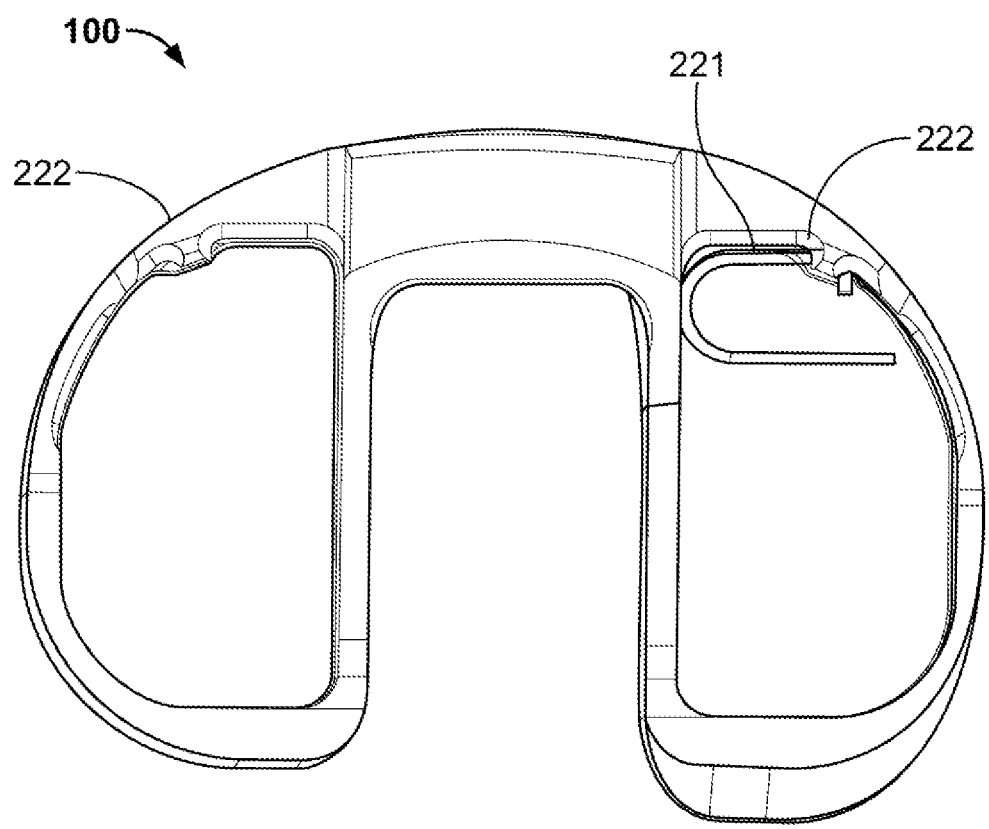

In other embodiments, as illustrated in FIGS. 8D-H, the locking mechanism may comprise a deflection ring 221 on the insert 200 and a tab 222 on the baseplate 100 to provide a robust locking mechanism. The deflection ring 221 is situated near an anterior portion of the insert 200 and part of the deflection protrudes from a recess in the insert 200. The deflection ring 221 is biased in the anterior direction, but has enough play to deflect in the opposite direction. The protruding portion of the deflection ring 221 is best illustrated in FIGS. 8F-G. As the insert 200 is positioned in the corresponding portion of the baseplate 100, an anterior tab 222 on the baseplate forces the deflection ring 221 backward. As insertion continues, the deflection ring 221 clears the anterior tab 222 and springs forward, locking the deflection ring under the anterior tab. The position of the deflection ring 221 in the locked position is illustrated in FIG. 8H with the insert 200 omitted. The robustness of this embodiment stems at least partially from the additional material of the ring and tab mechanism, as well as highly dispersion of loads over the additional material. The size and specific shapes of the anterior tab 221 and deflection ring 221 may be changed, for example, to alter the robustness of the locking mechanism.

In yet a further embodiment, a locking mechanism may include a deflecting wire 223 in the insert 200 and a corner recess 224 in the baseplate 100. The deflecting wire 223 is illustrated in FIG. 8I with the insert 200 omitted. Similar to the embodiment described in relation to FIGS. 8D-H, the deflecting wire 223 is positioned near the bottom of the insert with a corner portion 225 protruding from a recess in the baseplate 200. As the insert 200 is inserted into the baseplate 100, the corner portion 225 deflects backwards. As the insert 200 is further advanced, the corner portion 225 clears the baseplate 100 and springs back into a corner recess 224 in the baseplate. Two deflecting wires 223, one for each insert 200, are shown in the locked position in baseplate 100 in FIG. 8J with the inserts 200 omitted.

Figure 9A:
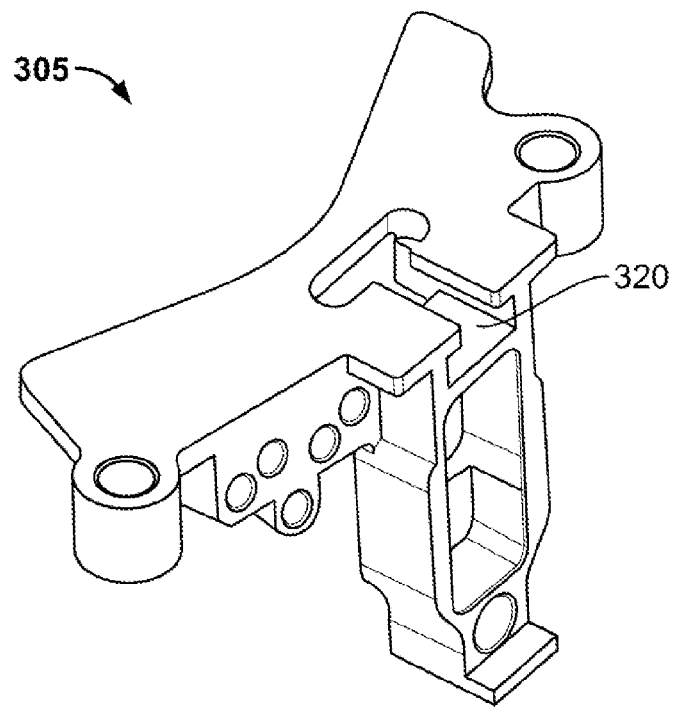
FIG. 9A illustrates a perspective view of a tibial resection guide.
Figure 9B:
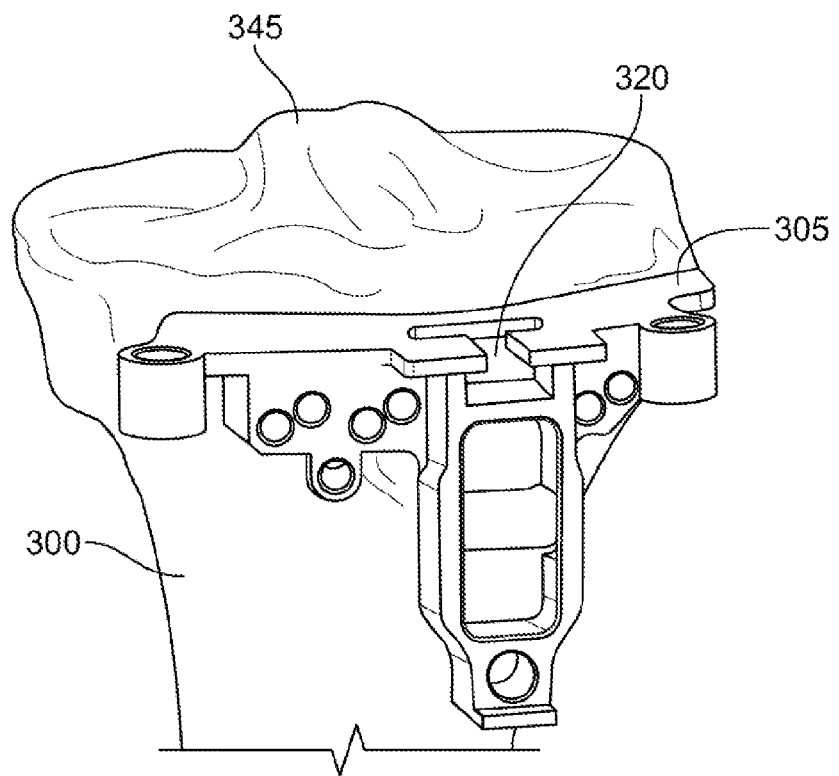
FIG. 9B illustrates the tibial resection guide of FIG. 9A positioned on a tibia.
Figure 10A:
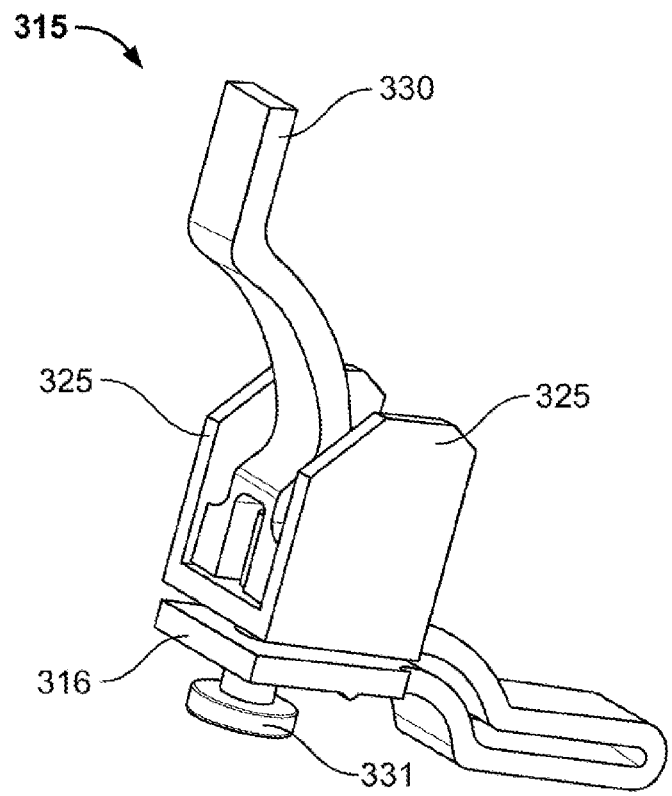
FIG. 10A illustrates a perspective view of a sagittal resection guide.
Figure 10B:
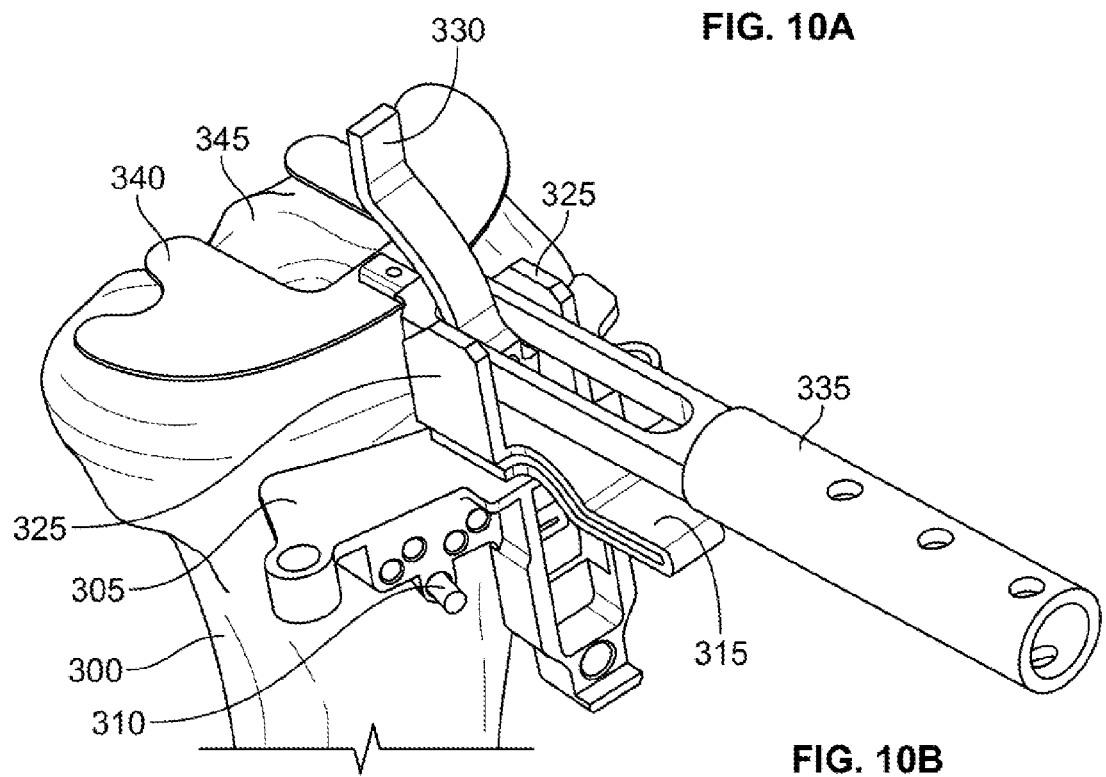
FIG. 10B illustrates a modular handle and the sagittal resection guide of FIG. 10A coupled to the tibial resection guide.

Prior to implanting the baseplate 100 onto the tibia 300, the tibia must be prepared. As illustrated in FIGS. 9A-B, a tibial resection guide 305 is first attached to the tibia 300. The positioning of the tibial resection guide 305 may be determined using, for example, an extramedullary or intramedullary alignment system, as is known in the art. Once the tibial resection guide 305 is in the desired position, it may be fixed to the tibia with the use of a fastener, such as one or more pins 310 (as shown in FIG. 10B). A sagittal cutting guide 315 (shown in FIG. 10A) is then attached to the tibial resection guide 305, for example by sliding a tab 316 of the sagittal cutting guide 315 into a slot 320 of the tibial resection guide.

The sagittal resection guide 315 may have multiple degrees of freedom of movement when coupled to the tibial resection guide 305 and in an unlocked position. For example, the sagittal cutting guide 315 may be translated in the ML and AP directions and rotated about an axis parallel to the longitudinal axis of the tibia 300. The sagittal cutting guide 315 may also include two walls 325 extending generally perpendicular from the sagittal cutting guide 315. The sagittal cutting guide 315 may also include a locking lever 330 to change the sagittal cutting guide 315 from a locked position to an unlocked position. In one embodiment, rotating the locking lever 330 anteriorly causes a button 331 to move superiorly, causing frictional locking engagement between the sagittal cutting guide 315 and the tibial resection guide 305.

Figure 11C:
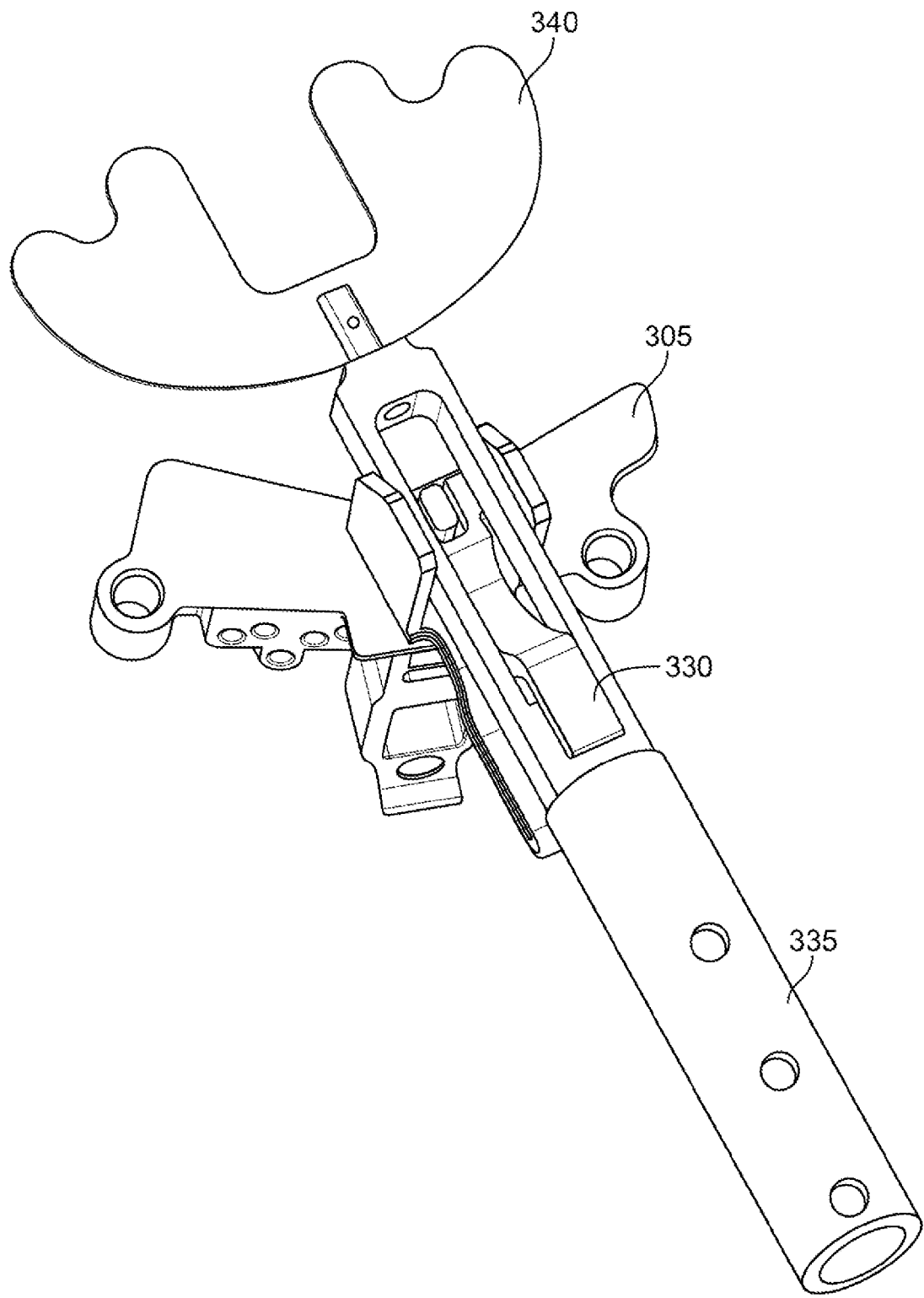
FIG. 11C illustrates the modular handle and template of FIG. 11A coupled to the tibial resection guide in a locked position.
Figure 12:
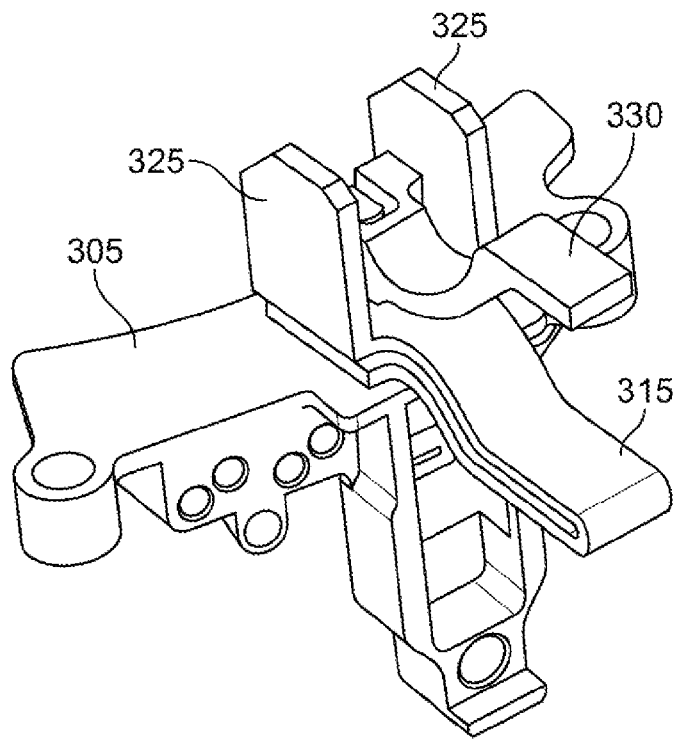
FIG. 12 illustrates an isolated perspective view of a sagittal resection guide in a locked configuration coupled to the tibial resection guide.
Figure 13:
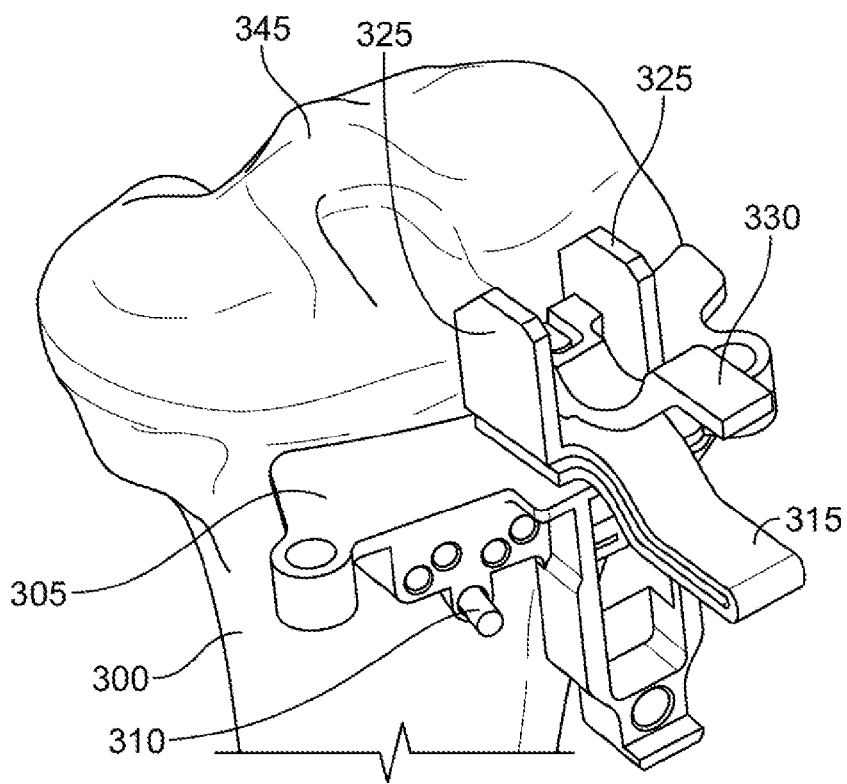
FIG. 13 illustrates a sagittal resection guide in the locked configuration coupled to the tibial resection guide.

A modular handle 335 with attached template 340, best seen in FIGS. 10B and 11A-B, may be attached to the sagittal cutting guide 315 over the locking lever 330. A slot 336 in the modular handle 335 is positioned over the sagittal cutting guide 325 such that the locking lever 330 is within the slot 336 and the walls of the modular handle 335 defining the slot 336 are adjacent to the walls 325 of the sagittal cutting guide 315. Using the modular handle 335, the surgeon may move the attached sagittal cutting guide 315 and template 340 until the template 340 desirably represents a position of the baseplate 100 to be implanted. The template 340 may come in a variety of sizes corresponding to differently sized baseplates 100 to help the surgeon determine the size of the baseplate 100 to be used. Once the surgeon is satisfied with the size and position of template 340 in relation to the tibia 300, he may rotate the locking lever 330 to lock the sagittal cutting guide 315 in its position, as best illustrated in FIG. 11C.

Figure 14:
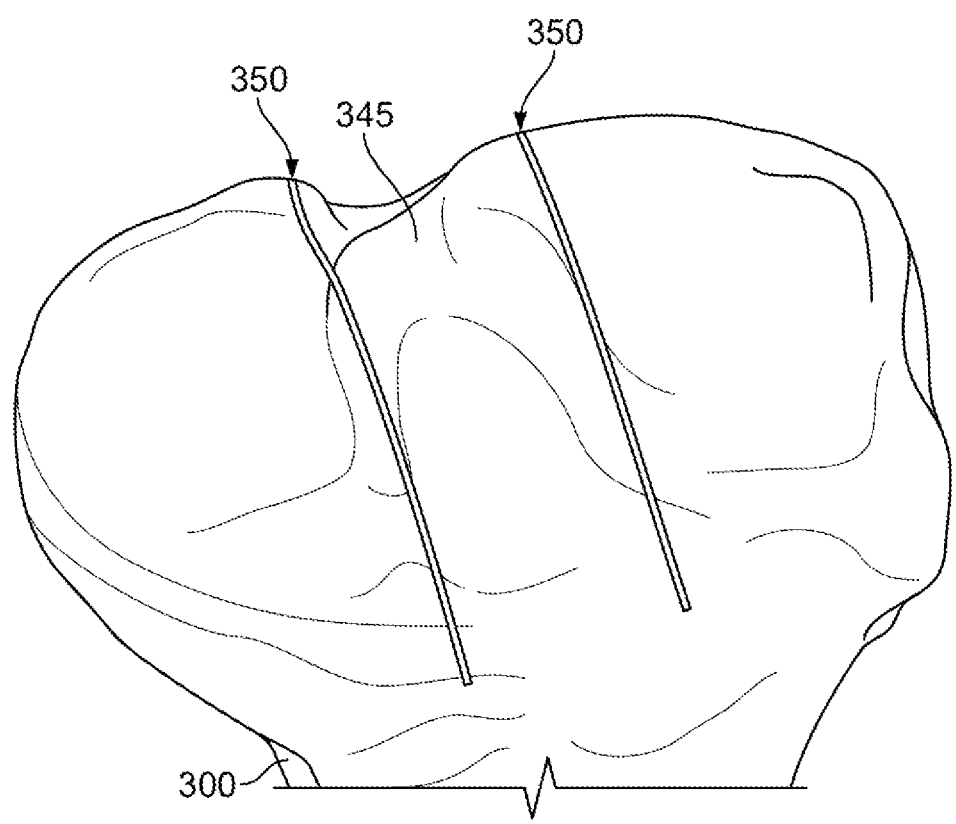
FIG. 14 illustrates an isolated perspective view of the proximal tibia after medial and lateral sagittal cuts are made.

Once locked in position, the modular handle 335 and template 340 may be removed (shown in FIGS. 12-13), and the surgeon may make the medial and lateral sagittal cuts 350, as shown in FIG. 14. To make the medial and lateral sagittal cuts 350, the surgeon uses a cutting tool, such as a reciprocating saw, using the walls 325 of the sagittal cutting guide 315 to guide the cuts. For example, the surgeon may slide the cutting tool along the outer surfaces of the walls 325 of the sagittal cutting guide 315 such that the medial and lateral sagittal cuts 350 flank the tibial eminence 345.

Figure 15A:
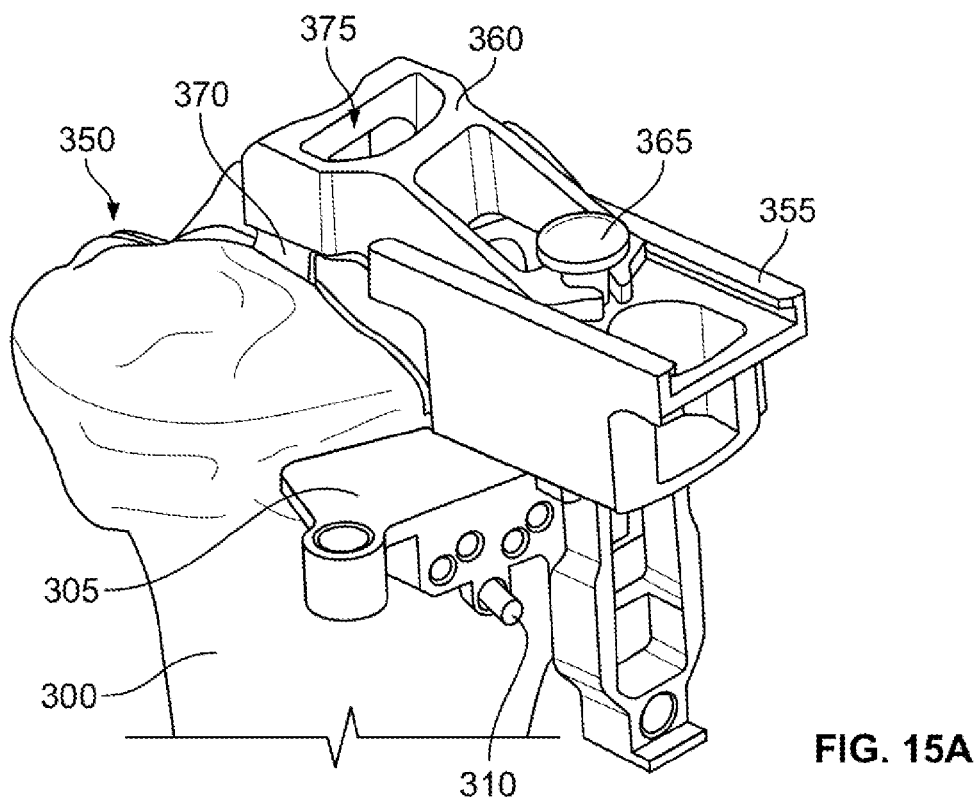
FIGS. 15A-B illustrate perspective and side views of an anterior block and punch guide coupled to the tibial resection guide and positioned on the tibia.
Figure 15B:
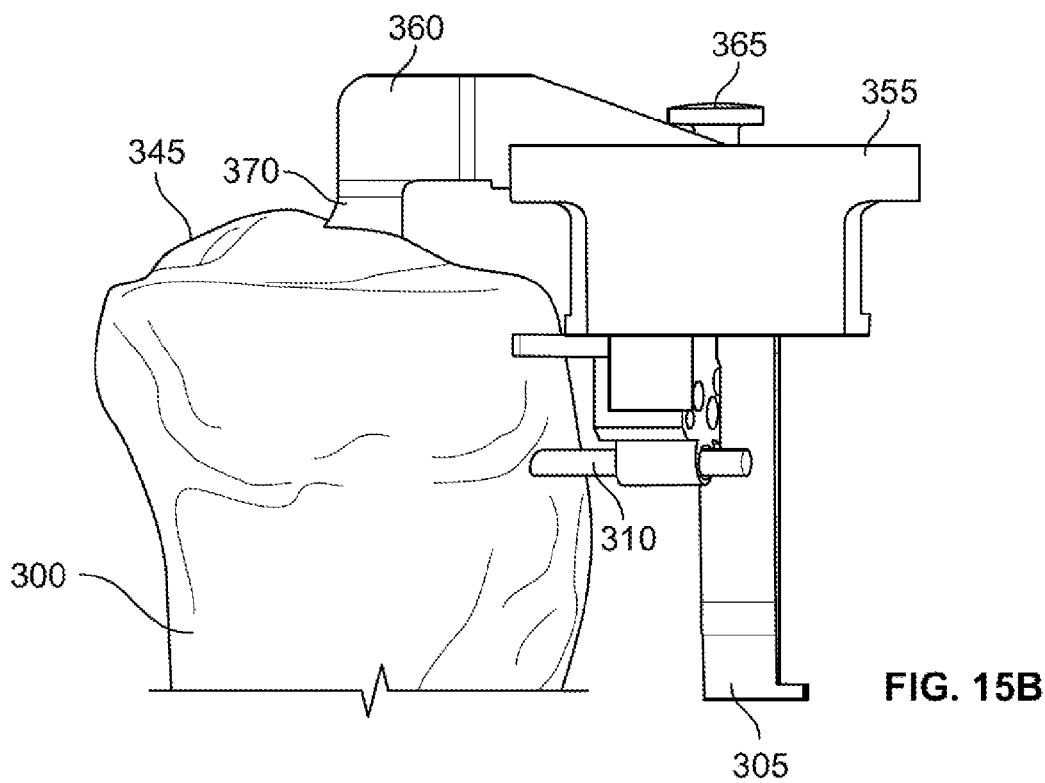

After the medial and lateral sagittal cuts 350 are made, the surgeon may remove the sagittal cutting guide 315 from the tibial resection guide 305 and insert in its place an anterior block 355 and attached punch guide 360, as illustrated in FIGS. 15A-B. The anterior block 355 is initially connected to the punch guide 360 with a fastener 365. The anterior block 355 and punch guide 360 are positioned such that feet 370 of the punch guide 360 are positioned with the medial and lateral sagittal cuts 350, the feet 370 flanking and protecting the tibial eminence 345. The distal portion of the anterior block 355 sits generally flush on the tibial resection guide 315 while an anterior portion of the anterior block 350 abuts the tibial cortex.

Figure 16A:
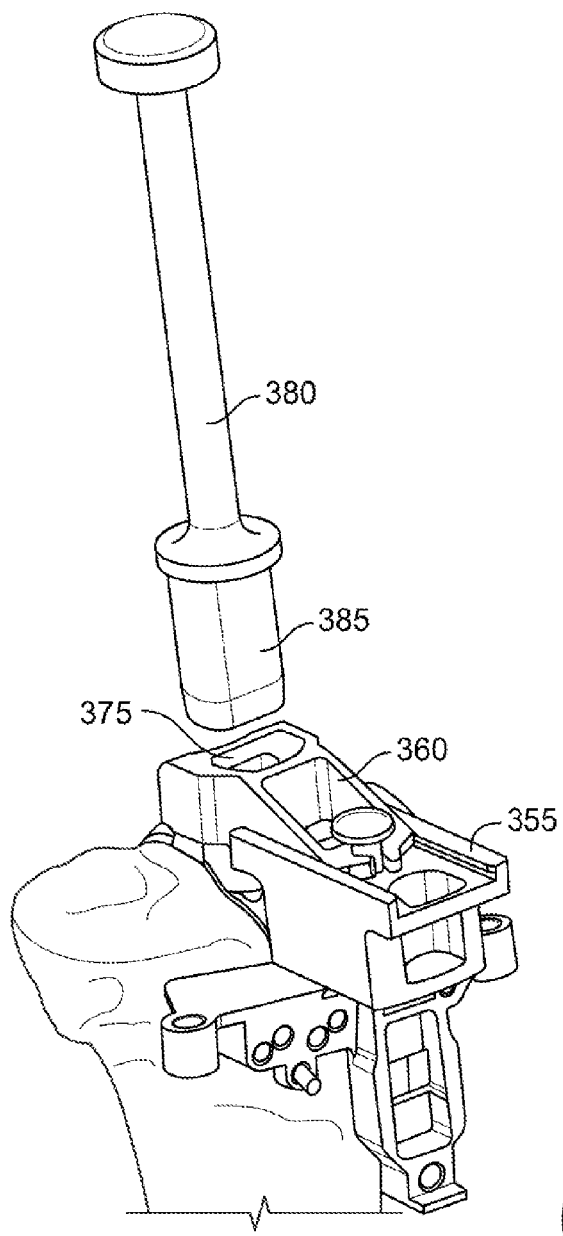
FIGS. 16A-C illustrate perspective views of a punch tower being used in conjunction with the punch guide in different stages of the punching process.
Figure 16B:
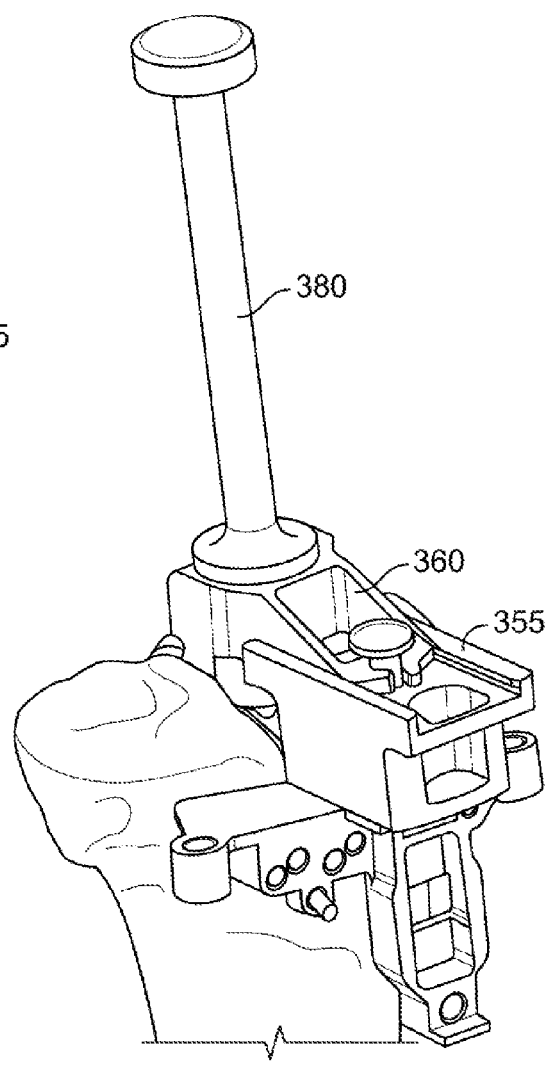
Figure 16C:
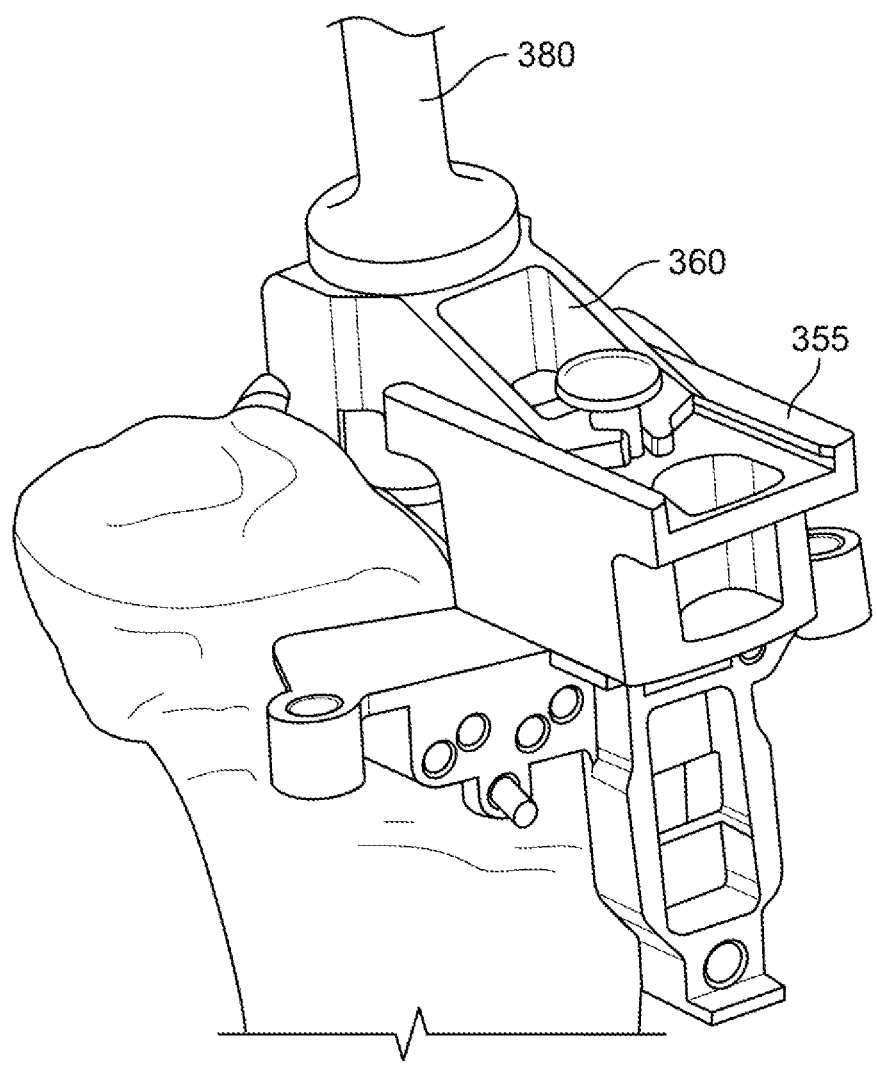

After the anterior block 355 and punch guide 360 are properly positioned, the surgeon may insert a punch 380 into the corresponding punch slot 375 of the punch guide 360, as illustrated in FIGS. 16A-C. Force is exerted on a proximal portion of the punch 380, for example by striking it with a hammer, such that a distal portion 385 of the punch 380 is driven into the tibial eminence 345. In one embodiment, the distal portion 385 of the punch 380 is generally hollow and includes straight medial and lateral portions that flank and protect the tibial eminence 345. The straight medial and lateral portions may be connected on the anterior side by a wall, with the posterior side of the distal portion 385 open. In this embodiment, the anterior wall of the distal portion 385 is configured to be driven into the tibial eminence 345, while the straight medial and lateral portions are configured to be positioned in the previously formed sagittal cuts 350. The posterior open portion of the distal portion 385 of the punch 380 prevents the punch 380 from cutting a posterior portion of the tibial eminence 345. In this embodiment, a transverse cross section of the distal portion 385 of the punch 380 is generally "U" shaped.

Figure 17:
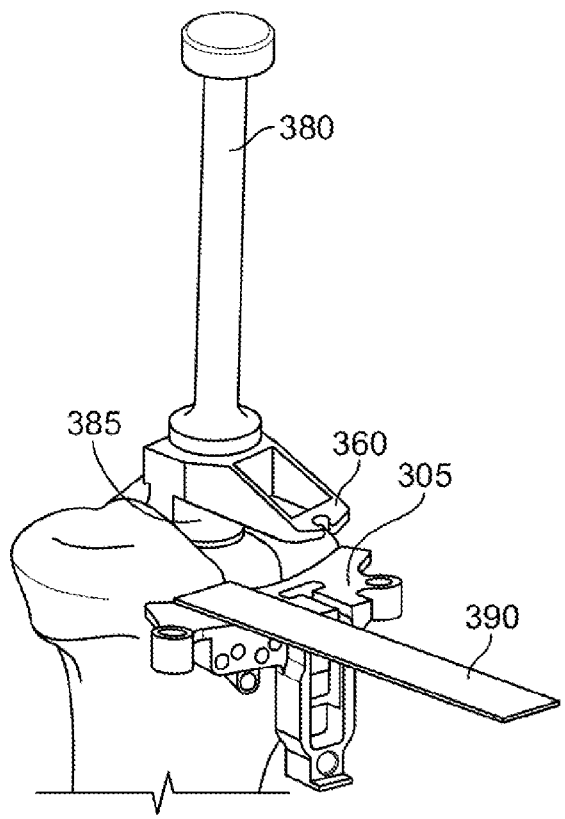
FIGS. 17-19 illustrate a cutting tool making a transverse tibial cut during different stages of the cut.

Once the punch 380 is driven into the tibia 300, as illustrated in FIG. 17, the anterior block 355 may be disengaged from the punch guide by depressing the fastener 365. The tibial resection guide 305 may also be removed from the bone.

Figure 18:
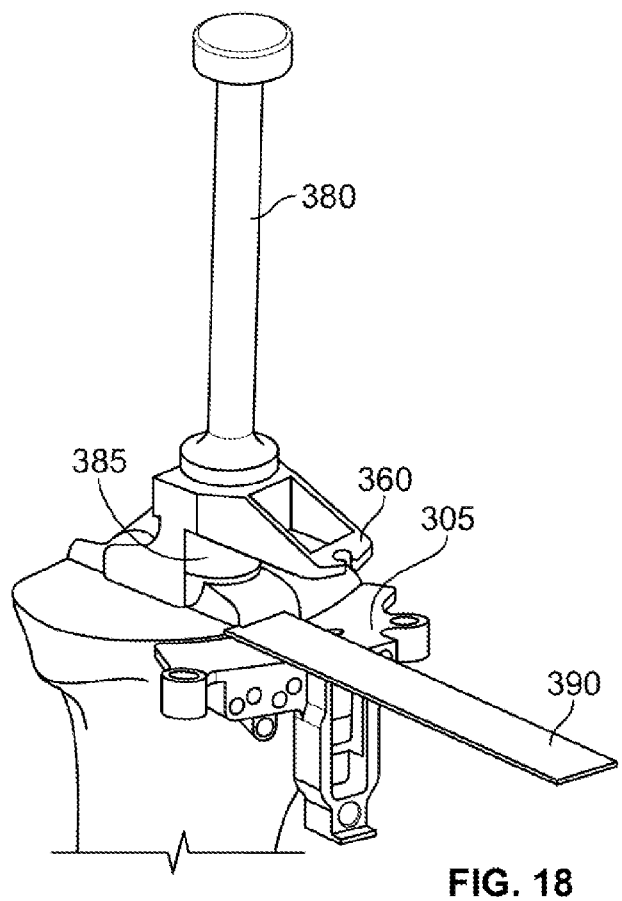
Figure 19:
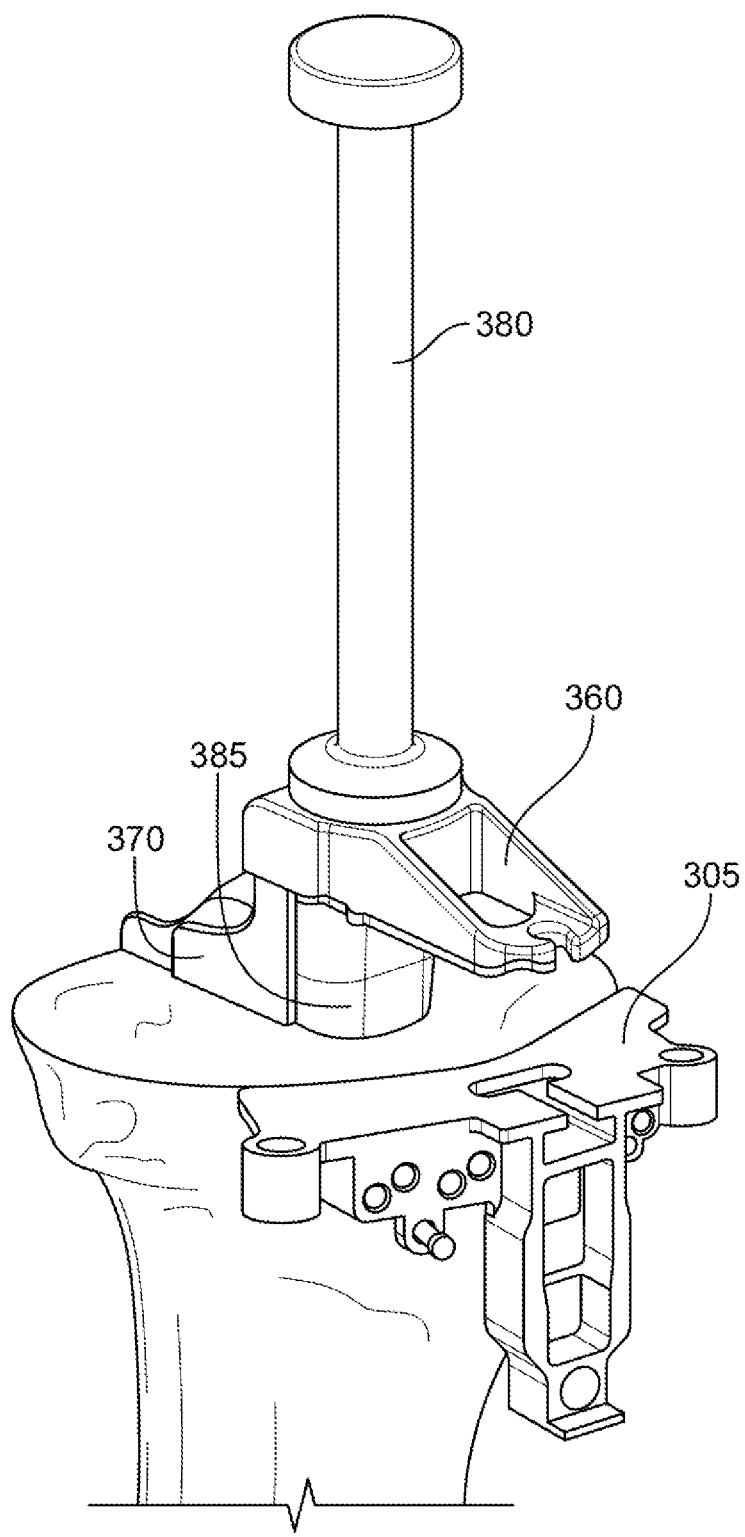
Figure 20A:
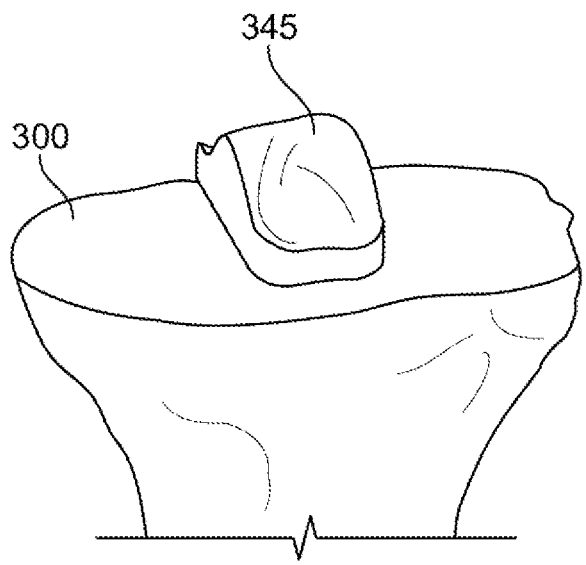
FIG. 20A illustrates an isolated perspective view of the proximal tibia after the transverse cut.

Once removed, the surgeon may use a use a cutting tool 390, such as a reciprocating saw, to make a transverse cut on the tibia 300. The surgeon may use the superior surface of the tibial resection guide 305 to guide the cut with the cutting tool 390. As the transverse cut is made, the distal portion 385 of the punch as well as the feet 370 of the punch guide 360 protect the tibial eminence 345 from being inadvertently cut. As shown in FIG. 18, the surgeon may make the medial and lateral transverse cuts on the tibia 300, and cut the anterior portion of the eminence 345 exposed outside of the distal portion 385 of the punch 380. The tibia 300 is illustrated in FIGS. 19-20A after the transverse cut is complete.

The dual use of the punch 380 as both a punching tool and a protector of the tibial eminence 345 during the transverse cut simplifies the surgical process by eliminating the need for an additional instrument during the bone cutting process. The punch guide 360 and the punch 380 may also accommodate an angle of between approximately 0°-45°, preferably about 20°, from the resection plane that corresponds with the angle of the posterior wall of the anterior bridge 115 (described above with respect to FIG. 4B). The corresponding angle, as described above, allows the baseplate 100, once implanted, to counteract forces exerted by the ACL that pull the tibial eminence 345 upward. The angular punching may also enhance the bone strength of the tibial eminence 345 by retaining more bone and providing a cement buttress against the eminence bone.

Figure 20B:
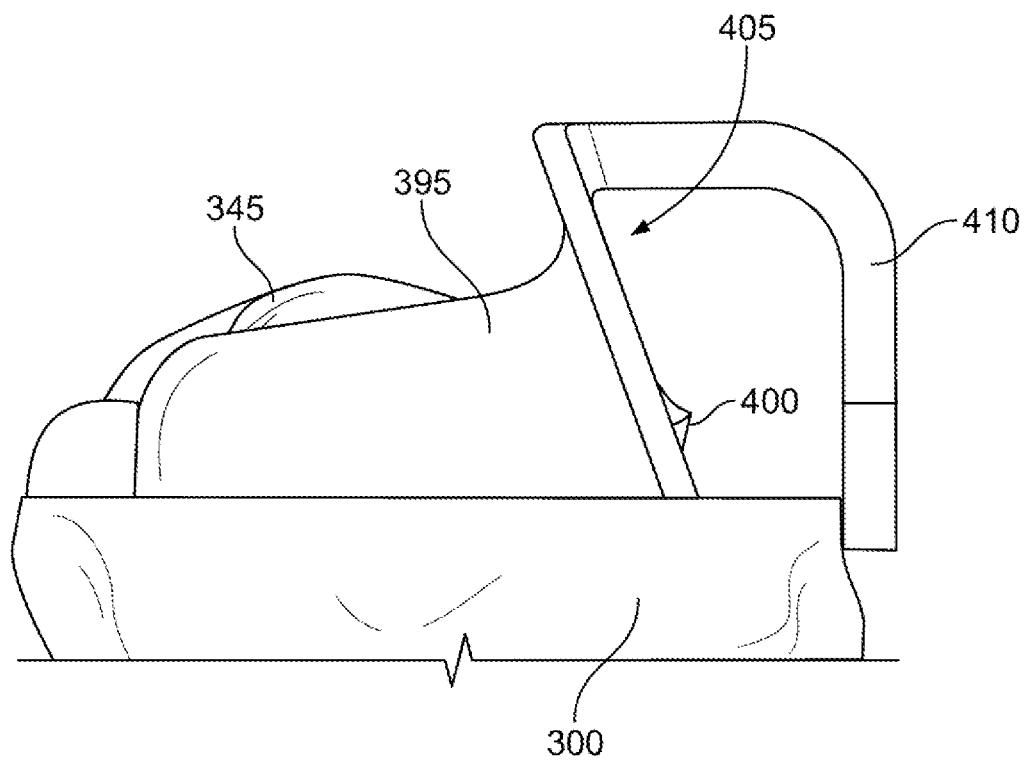
FIGS. 20B-C illustrate side and perspective views of an anterior chamfer cut guide positioned on the tibia.
Figure 20C:
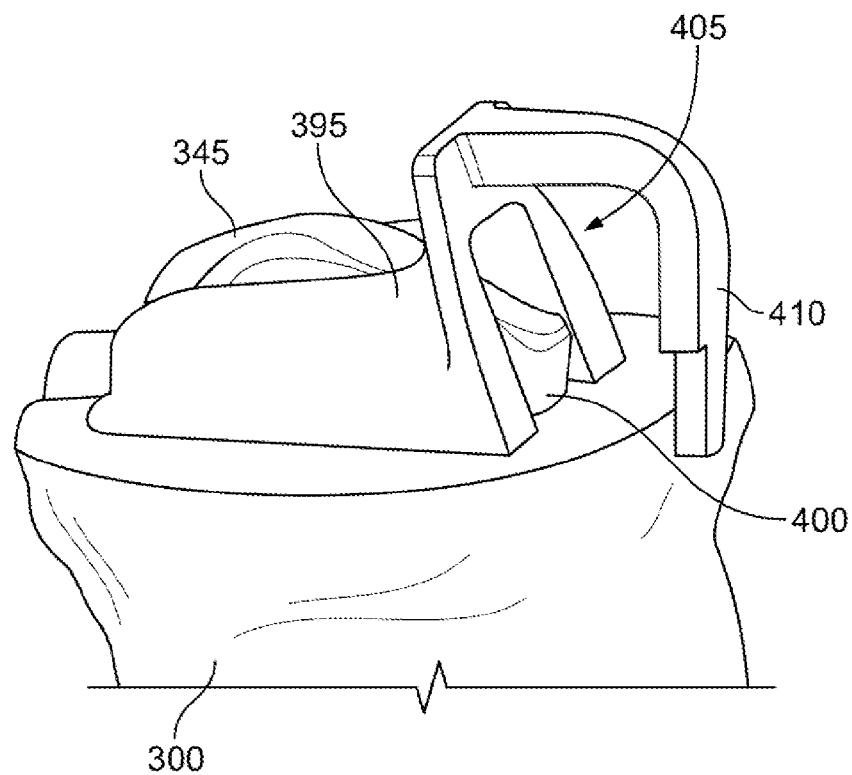
Figure 21:
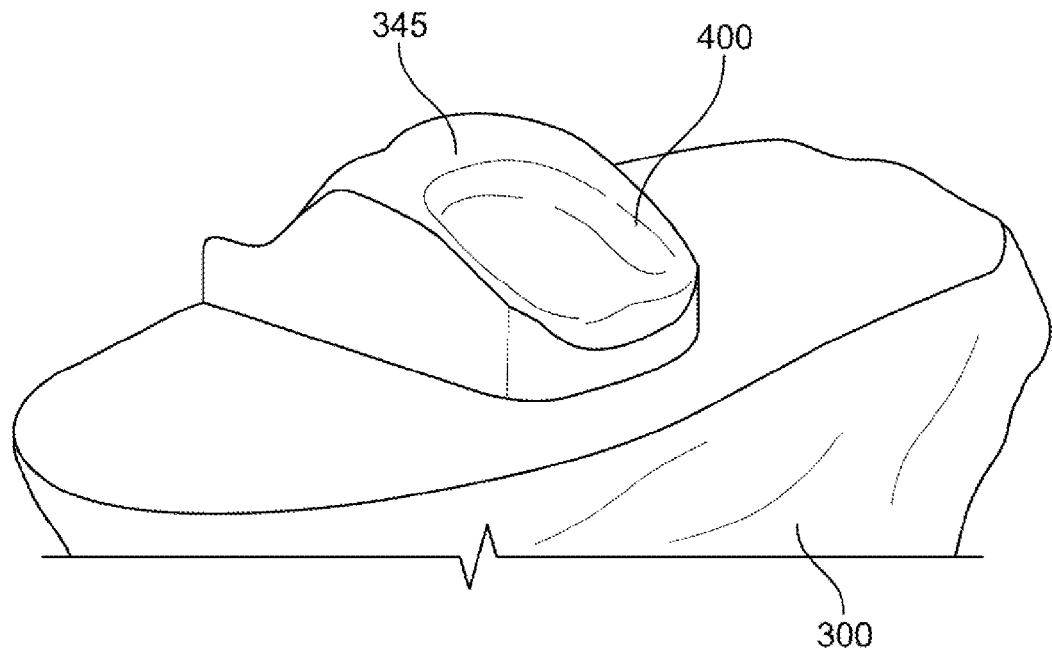
FIG. 21 illustrates an isolated perspective view of the proximal tibia after an anterior chamfer cut.

After the transverse resection is complete, an anterior chamfer cut guide 395 may be positioned on the resection surface of the tibia, as illustrated in FIGS. 20B-C. The anterior chamfer cut guide 395 is positioned such that an anterior extension 410 rests on the anterior cortex of the tibia 300. If an anterior portion 400 of the tibial eminence 345 protrudes beyond the angled cutting surface 405 of the anterior chamfer cut guide 395, the surgeon may cut the anterior portion 400 of the eminence 345 with a cutting tool. The anterior portion 400 of the eminence 345 after the chamfer cut is made is illustrated in FIG. 21.

Figure 22:
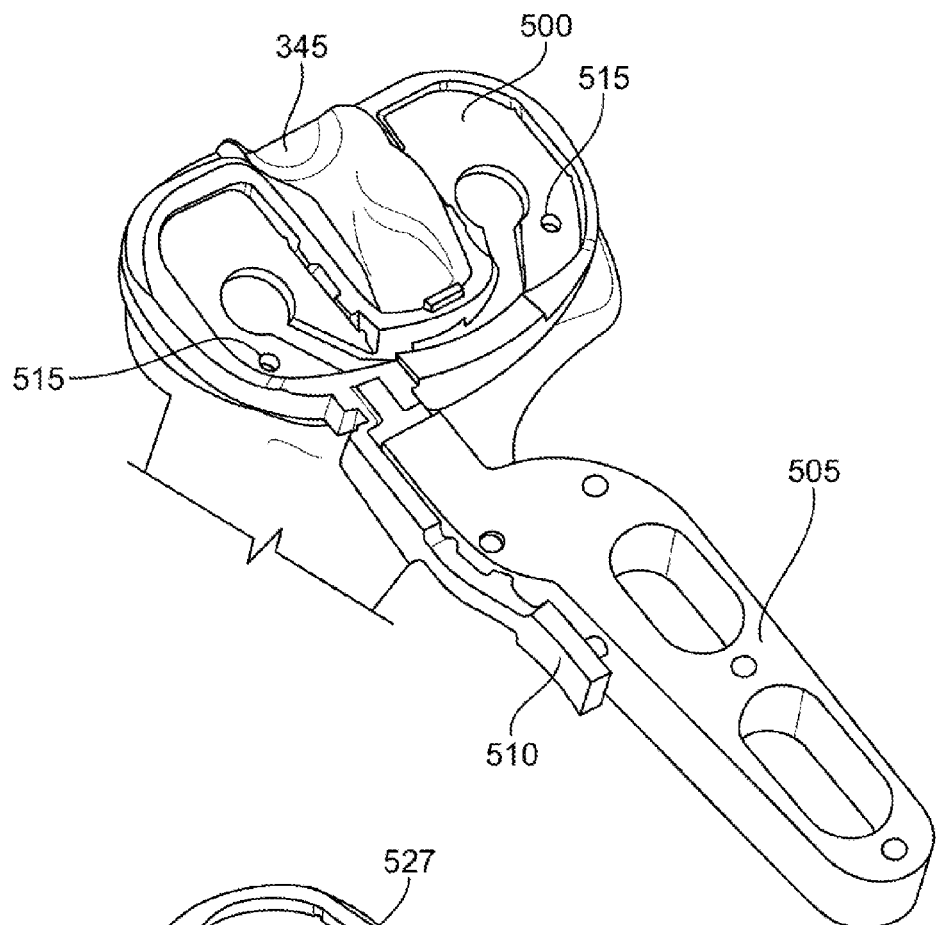
FIG. 22 illustrates a perspective view of a tibial baseplate trial positioned on the tibia according to an aspect of the invention.
Figure 23:
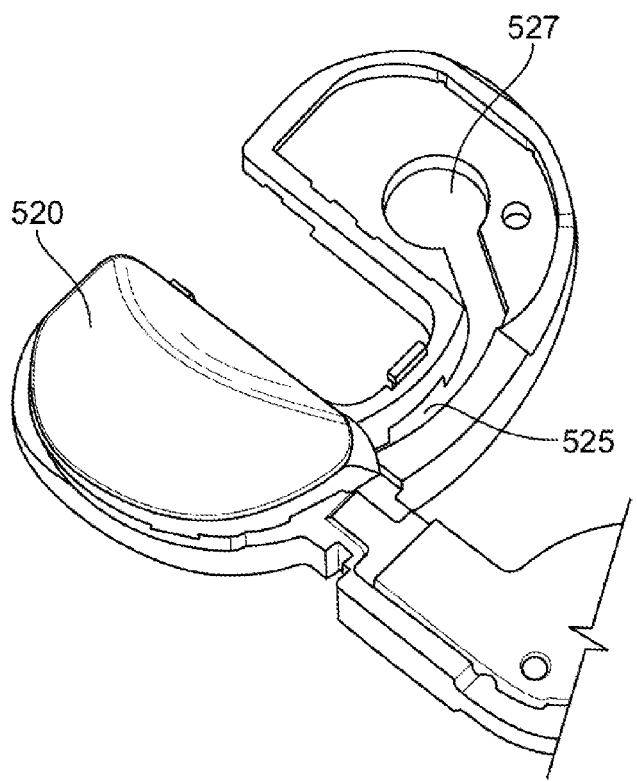
FIG. 23 illustrates an isolated perspective view of the tibial baseplate trial of FIG. 22 with a trial insert.

With the transverse resection and optional chamfer cut complete, trial sizing begins. As illustrated in FIG. 22, a tibial template 500 may be connected to a handle 505. The tibial template 500 is fit on the resected tibia 300. A variety of different sized tibial templates 500 may be connected to the handle 505. The tibial templates 500 may be connected and disconnected from the handle 505 using a lever 510. The differently sized tibial templates 500 generally correspond to the differently sized baseplates 100. The tibial template 500 may also include fixing apertures 515, through which a fastener may be inserted into the tibia 300 to temporarily fix the tibial template 500 to the tibia 300. The surgeon chooses the best fitting tibial template 500 that addresses rotation and coverage of the resected tibia 300.

Once the surgeon is satisfied with the chosen tibial template 500, a pair of trial inserts 520 (only one shown in FIG. 23) is coupled to the tibial template 500. The trial insert 520 generally corresponds to the inserts 200 described above. Before or after the trial inserts 520 and tibial template 500 are in place, the surgeon may also attach a femoral trial onto the femur which had been prepared earlier during surgery. With the trial inserts 520, tibial template 500, and trial femoral components in place, the surgeon may bring the knee through a range of motion to determine if the final seating position of the implant would be satisfactory.

Figure 24:
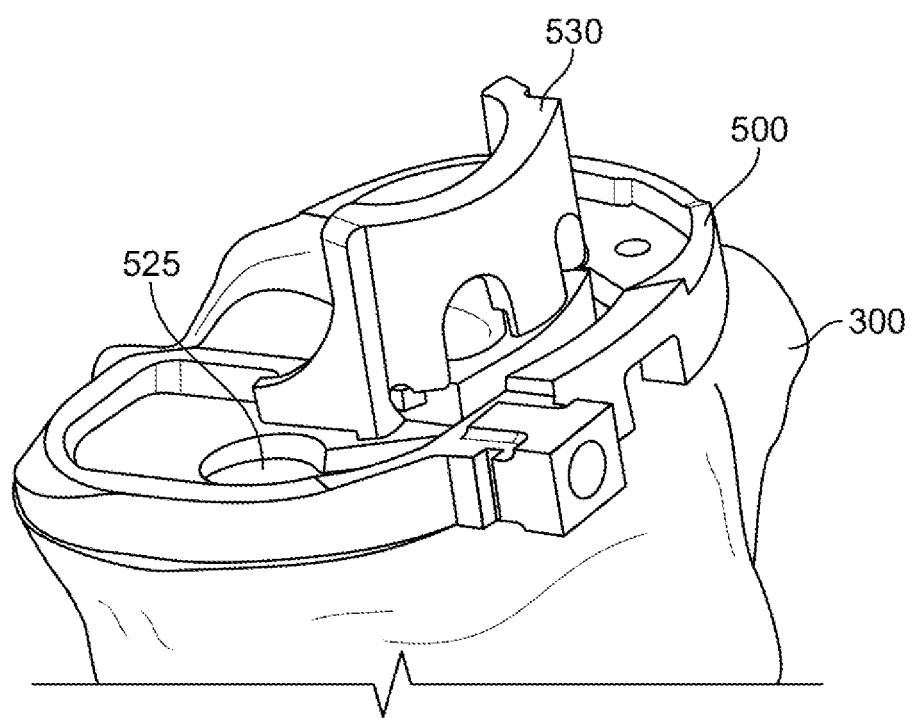
FIG. 24 illustrates a perspective view of a keel punch tower coupled to a tibial baseplate trial.
Figures 25A, 25B:
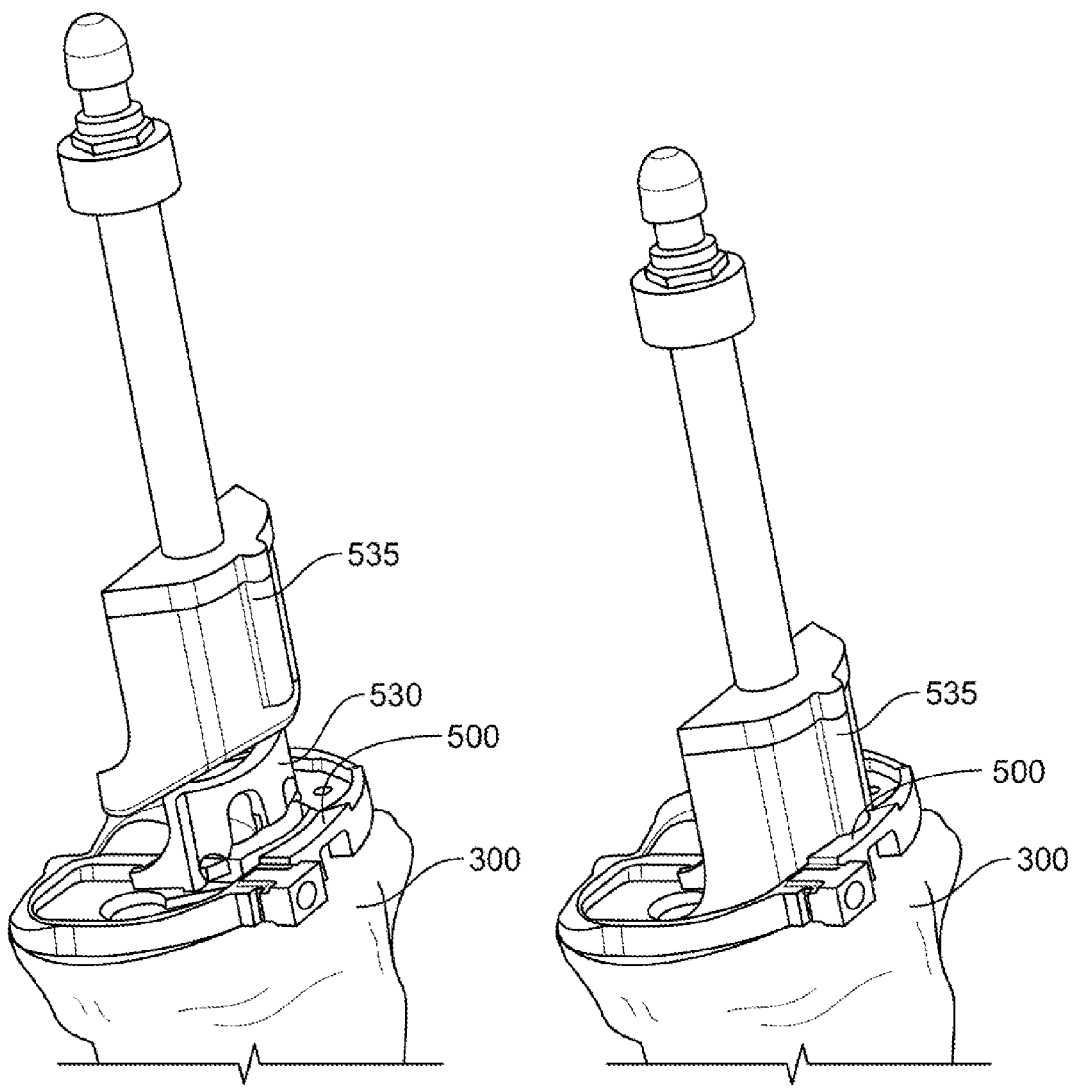
FIGS. 25A-B illustrate perspective views of a first keel punch during different stages of a first keel punch.
Figure 25C:
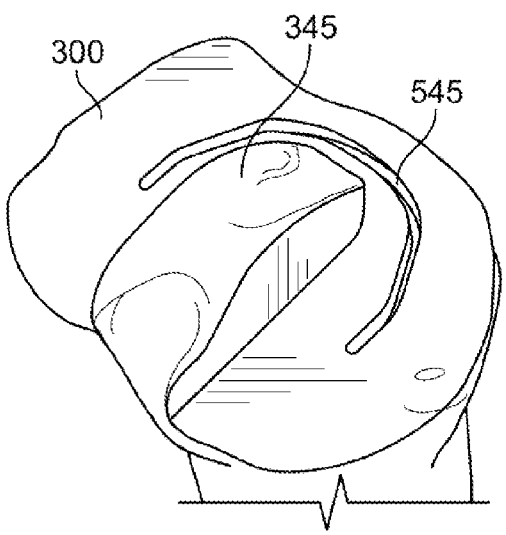
FIG. 25C illustrates an isolated perspective view of the proximal tibia after the first keel punch is complete.
Figures 26A, 26B:
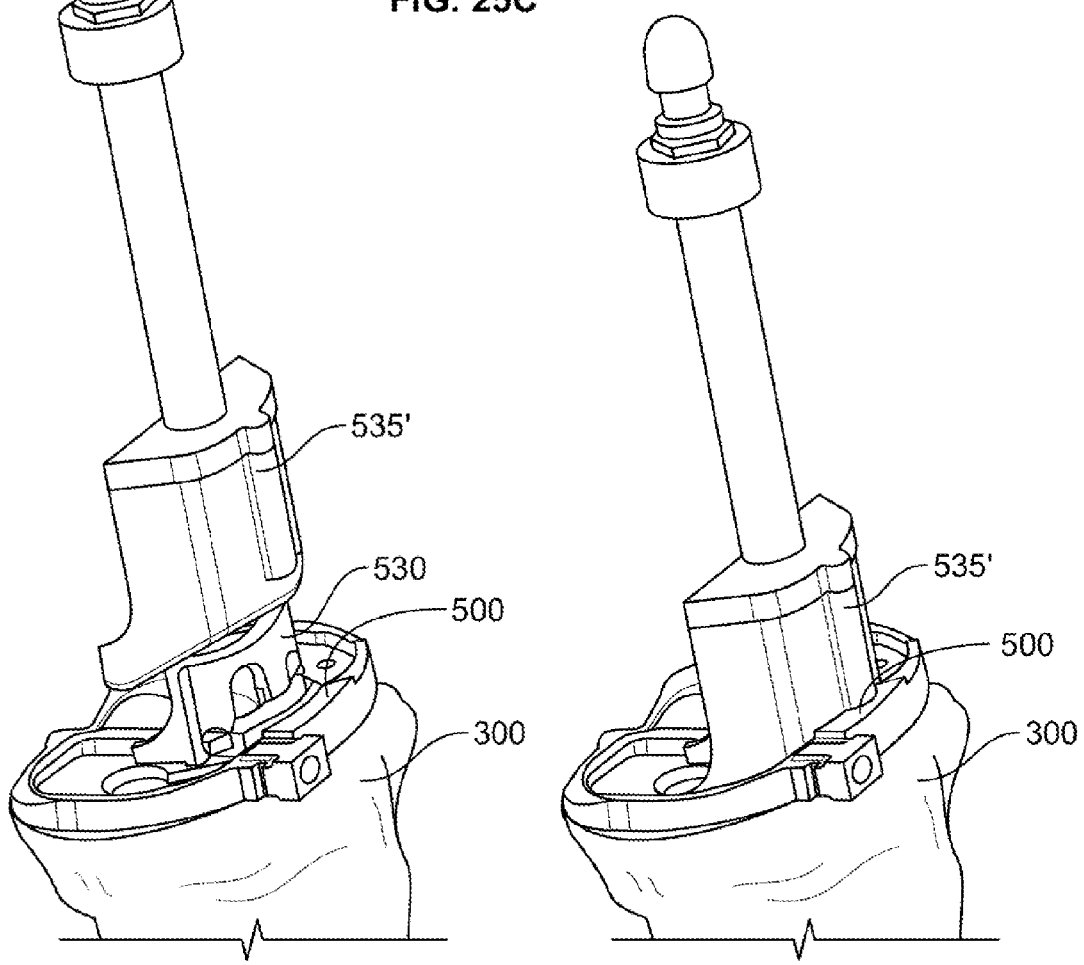
FIGS. 26A-B illustrate perspective views of a second keel punch during different stages of a second keel punch.
Figure 26C:
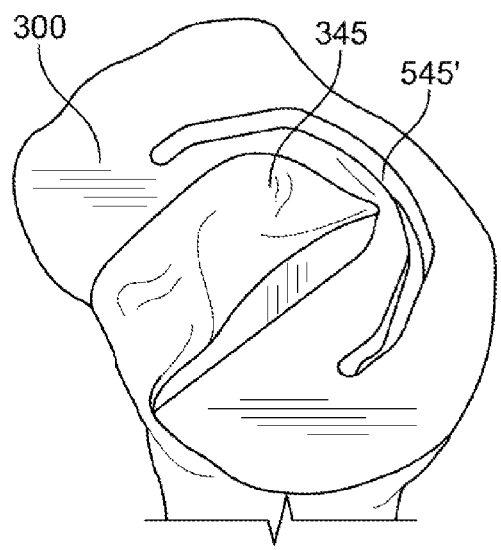
FIG. 26C illustrates an isolated perspective view of the proximal tibia after the second keel punch is complete.

Once size and rotation have been confirmed, the trial inserts 520 are removed and the surgeon may perform the keel punch. A keel punch tower 530 is attached to the tibial template 500, as illustrated in FIG. 24. A first keel punch 535 is positioned over the keel punch tower 530, as illustrated in FIG. 25A. Once in position, the keel punch 535 is driven into the tibia, as illustrated in FIG. 25B, for example by striking the keel punch 535 with a hammer. When struck, the first keel punch 535 drives through the keel recess 525 of the tibial template 500 (illustrated in FIG. 23) and into the tibia 300. The tibia 300 and tibial keel recess 545 after the first keel punch is performed are illustrated in FIG. 25C. After the first keel punch is complete, a second keel punch is performed. As illustrated in FIGS. 26A-B, the keel punch process is repeated, except that the second keel punch 535' is larger than the first keel punch 535. As illustrated in FIG. 26C, the tibial keel recess 545' in the tibia 300 is enlarged after the second keel punch. By forming the keel recess 545' in sequential keel punching steps, with a first smaller keel punch and a second larger keel punch, the likelihood of fracturing the anterior tibia is reduced. Sequential keel punching may be especially preferred in embodiments in which the keel 125 of the baseplate 100 is relatively thick and high forces for keel punching are required to create a large tibial keel recess 545'.

Figure 27A:
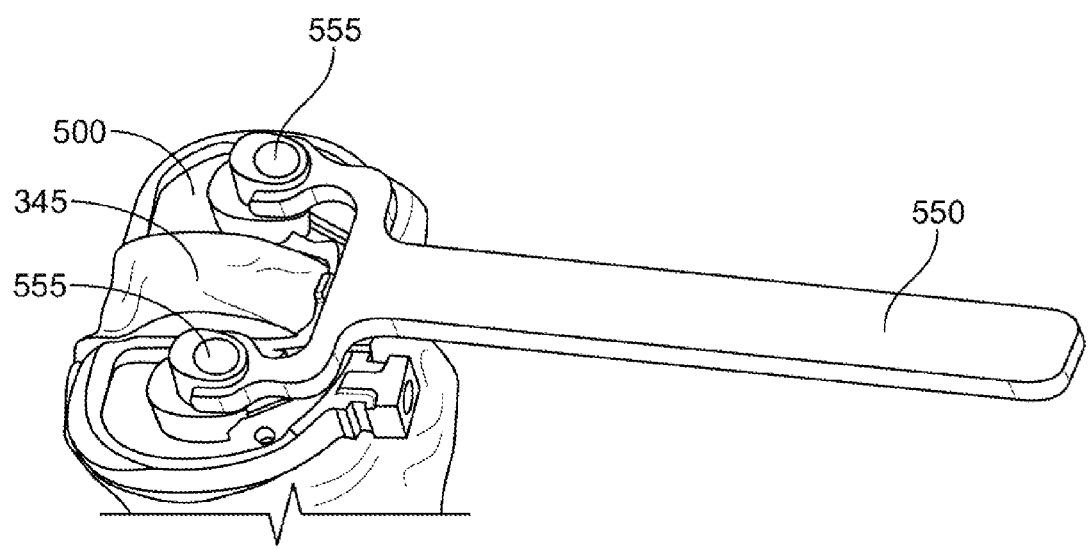
FIG. 27A illustrates a tool with peg drill bushings coupled to the trial tibial baseplate.
Figure 27B:
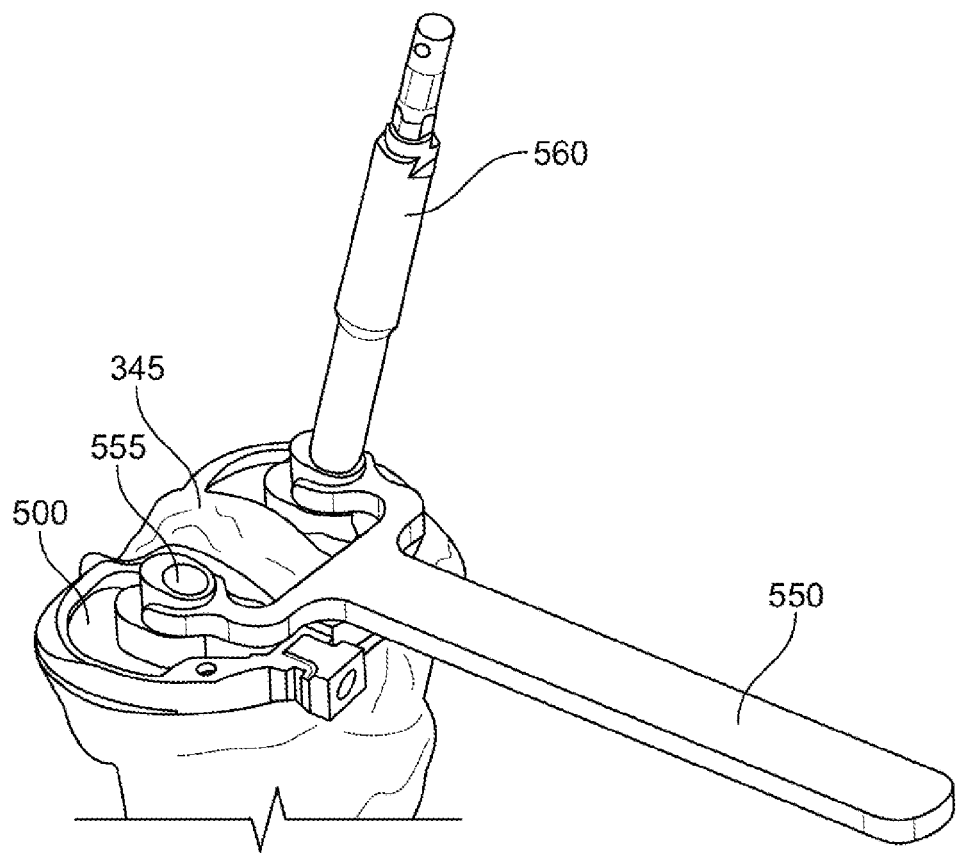
FIG. 27B illustrates a drilling step with a drill positioned in the peg drill bushings of FIG. 27A.
Figure 27C:
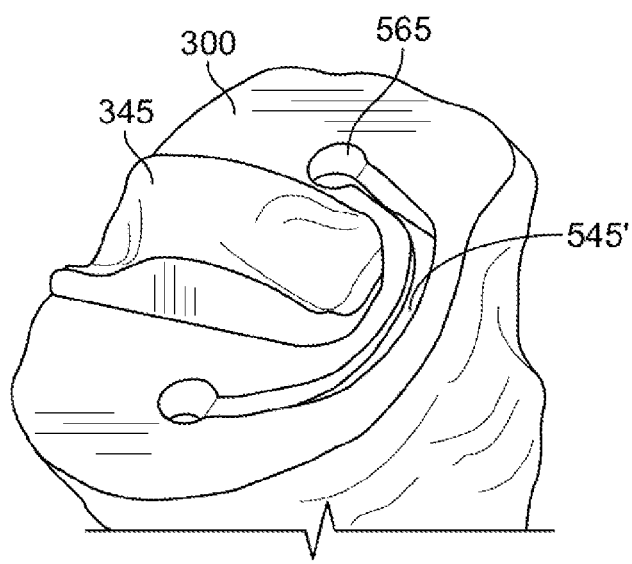
FIG. 27C illustrates an isolated perspective view of the proximal tibia after the peg drilling is complete.

After the keel punches are complete, a tool 550 with peg drill bushings 555 is positioned on the tibial template 500, as illustrated in FIG. 27A. The peg drill bushings 555 are coupled to the peg drill slots 527 in the tibial template 500 (illustrated in FIG. 23). With the tool 550 in place, a drill 560 or other cutting device is inserted through the peg drill bushings 555 to form the peg recesses 565 in the tibia 300 (illustrated in FIG. 27C).

For the above described keel punch and peg drilling steps, the size of the recesses created generally corresponds to the size of the keel 125 and pegs 130, 135 in the baseplate 100 to be implanted. As is known in the art, the keel 125 and pegs 130, 135 may be additionally fixed to the tibia with cement or other adhesive. When using cement, it may be preferable to create a keel recess 545' that is slightly larger than the keel 125, and peg recesses 565 that are slightly larger than the pegs 130, 135, such that a cement mantle is provided. In one embodiment, the cement mantle is between approximately 0 mm-0.75 mm, preferably about 0.5 mm.

Figure 28:
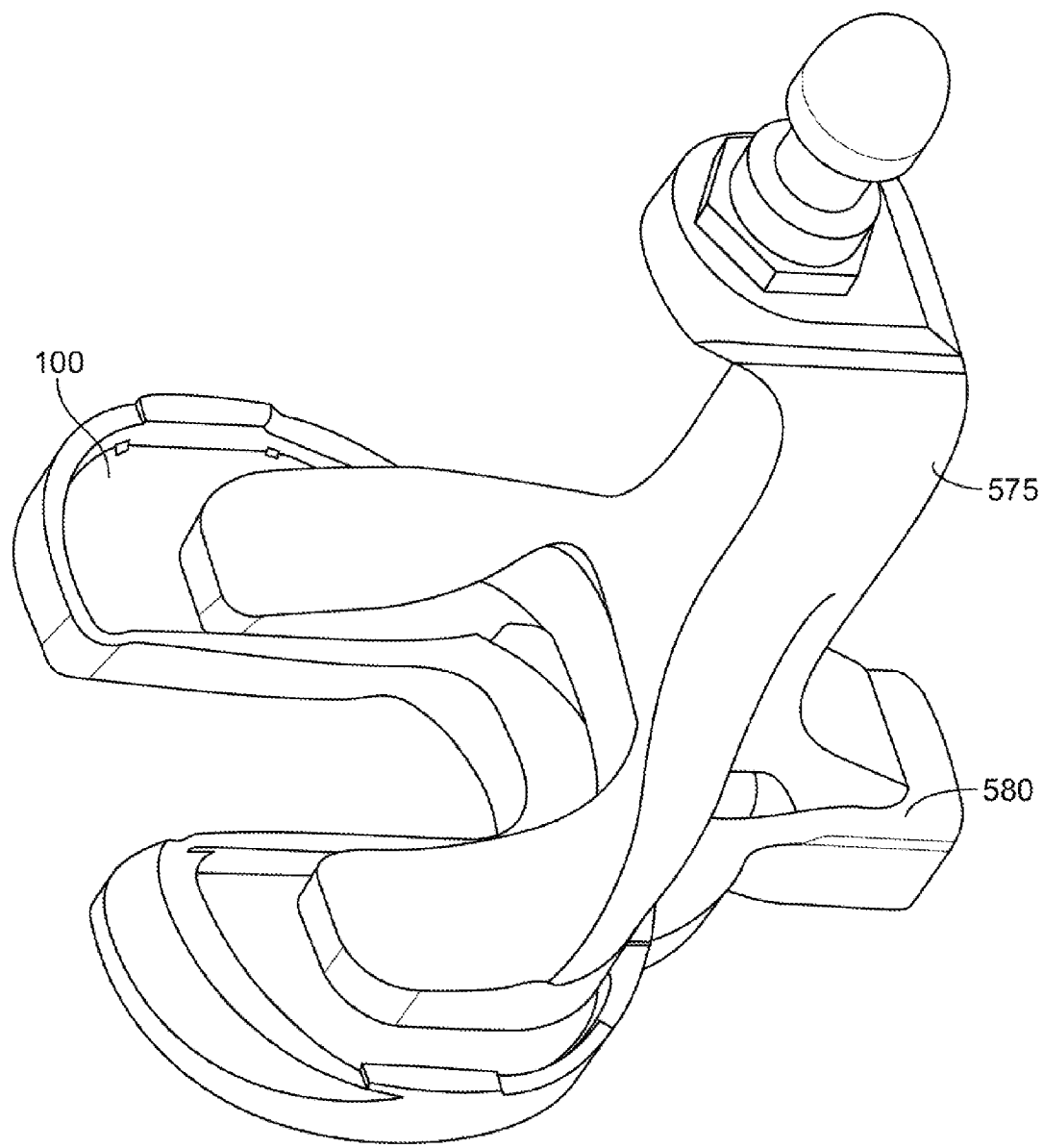
FIG. 28 illustrates an isolated perspective view of a tibial baseplate impactor coupled to a tibial baseplate.

After the tibia 300 is fully prepared, the baseplate 100 may be implanted into the tibia 300. As illustrated in FIG. 28, the baseplate 100 is connected to a baseplate impactor 575. A connector portion 580 of the baseplate impactor 575 may connect to the anterior portion of baseplate 100, for example, with a pair of prongs or other connecting mechanism (not illustrated). The baseplate 100 is positioned on the tibia 300, with the keel 125 proximate the tibial keel recess 545' and the fixation pegs 130, 135 proximate the tibial peg recesses 565. If desired, cement or other adhesives may be applied to the keel 125 and/or fixation pegs 130, 135. Cement may also be applied to the tibial bone surface and/or the tibial keel recess area. Once in place, the baseplate 100 may be driven into the tibia 300, for example by striking the baseplate impactor 575 with a hammer. The baseplate impactor 575 is disengaged from the tibial baseplate 100, and the tibial implant implantation is complete.

Some or all of the tibial preparation techniques, including resection, keel punching, and peg drilling, may be performed manually by the surgeon. Additionally, some or all of the tibial preparation techniques may be performed with robotic instruments. Utilizing robotic instruments along with surgeon supervision is generally preferred. For example, in one embodiment, a robotic tool may be guided within a certain limit of pre-defined constraints. For example, a robotic cutting tool may be used by a surgeon to perform the tibial resection, with a set of dimensional constraints such that the surgeon is free to operate the cutting tool, but only within a predefined space. If the cutting tool reaches the limit of the predefined space, the tool may limit itself from moving further in that direction if it would exit the predefined space. The precision and consistency resulting from the use of robotic instruments in the preparation of the tibia may reduce the time of surgery while improving postoperative results. Such robotic instruments and methods of using robotic instruments for implantation are further described in U.S. patent application Ser. No. 13/608,888, filed Aug. 31, 2012, U.S. Patent Application No. 61/679,258, filed Aug. 3, 2012, and U.S. Patent Publication No. 2012/0330429, filed Jun. 22, 2012. The contents of the three above referenced applications are hereby incorporated herein in their entirety.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. Similarly, different aspects described herein may be combined with other aspects in various ways while remaining within the scope of the invention.

The invention claimed is:

1. A bicruciate retaining tibial implant baseplate comprising:
   a superior surface;
   a bone contacting surface;
   a lateral condylar portion;
   a medial condylar portion spaced from the lateral condylar portion defining an opening therebetween;
   a bridge portion connecting the medial and lateral condylar portions at an anterior end portion of the baseplate;
   a keel extending inferiorly from the bone contacting surface of the baseplate and having an anterior portion and posterior portions, an inferior edge of the keel continuously sloping with respect to the bone contacting surface of the baseplate from an anteriormost end to a posteriormost end so that thea posteriormost end of the keel extends from the bone contacting surface farther inferiorly than the anteriormost end of the keel, and the keel extending from the lateral condylar portion across the bridge portion to the medial condylar portion;
   a cylindrical lateral fixation peg proximate a lateral end of the keel and extending inferiorly from the bone contacting surface; and
   a cylindrical medial fixation peg proximate a medial end of the keel and extending inferiorly from the bone contacting surface.

2. The bicruciate retaining tibial implant baseplate of claim 1, wherein the bridge portion of the baseplate includes an angled posterior wall portion positioned superior to the keel, the angled posterior wall portion being substantially uniformly angled such that an inferior portion of the angled posterior wall is positioned anterior to a superior portion of the angled posterior wall, the angled posterior wall configured to contact an angled surface of a tibial eminence when implanted.

3. The bicruciate retaining tibial implant baseplate of claim 2, wherein the angled posterior wall of the baseplate is angled between 5 and 45 degrees with respect to the bone contacting surface of the baseplate.

4. The bicruciate retaining tibial implant baseplate of claim 3, wherein the angled posterior wall of the baseplate is angled between 15 and 25 degrees with respect to the bone contacting surface of the baseplate.

5. The bicruciate retaining tibial implant baseplate of claim 1, further comprising:
   a medial insert configured to be inserted into the medial condylar portion of the baseplate; and
   a lateral insert configured to be inserted into the lateral condylar portion of the baseplate.

6. The bicruciate retaining tibial implant baseplate of claim 5, wherein at least one of the medial and lateral inserts includes a spring connected to a pin, the spring biasing the pin, the pin being configured to mate with a corresponding pin aperture of the baseplate to lock the insert to the baseplate.

7. The bicruciate retaining tibial implant baseplate of claim 5, wherein at least one of the medial and lateral inserts includes a relief portion on a medial side of the insert, the relief portion increasing in size from an anterior portion of the insert toward a posterior portion of the insert.

8. The bicruciate retaining tibial implant baseplate of claim 1, wherein the medial condylar portion has an anterior-posterior dimension and the lateral condylar portion has an anterior-posterior dimension, the anterior-posterior dimension of the medial condylar portion being larger than the anterior-posterior dimension of the lateral condylar portion.

9. The bicruciate retaining tibial implant baseplate of claim 8, wherein the anterior-posterior dimension of the medial condylar portion is between 1 and 6 millimeters larger than the anterior-posterior dimension of the lateral condylar portion.

10. The bicruciate retaining tibial implant baseplate of claim 9, wherein the anterior-posterior dimension of the medial condylar portion is between 3 and 5 millimeters larger than the anterior-posterior dimension of the lateral condylar portion.

11. The bicruciate retaining tibial implant baseplate of claim 1, wherein the lateral fixation peg is positioned at a terminal end of the lateral end of the keel.

12. The bicruciate retaining tibial implant baseplate of claim 1, wherein the medial fixation peg is positioned at a terminal end of the medial end of the keel.

* * * * *